United States Patent
Khonsari et al.

(10) Patent No.: US 11,994,505 B2
(45) Date of Patent: *May 28, 2024

(54) PEANUT BUTTER EVALUATION

(71) Applicants: Michael M. Khonsari, Baton Rouge, LA (US); Lijesh Koottaparambil, Baton Rouge, LA (US)

(72) Inventors: Michael M. Khonsari, Baton Rouge, LA (US); Lijesh Koottaparambil, Baton Rouge, LA (US)

(73) Assignee: Bd. of Supervisors of La. St. Univ. & A&M College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/340,723

(22) Filed: Jun. 23, 2023

(65) Prior Publication Data
US 2023/0408484 A1     Dec. 21, 2023

Related U.S. Application Data

(63) Continuation of application No. 17/467,019, filed on Sep. 3, 2021, now Pat. No. 11,686,719.

(60) Provisional application No. 63/074,574, filed on Sep. 4, 2020.

(51) Int. Cl.
| | |
|---|---|
| *G01N 33/28* | (2006.01) |
| *G01N 1/10* | (2006.01) |
| *G01N 1/28* | (2006.01) |
| *G01N 13/02* | (2006.01) |

(52) U.S. Cl.
CPC ........... *G01N 33/2888* (2013.01); *G01N 1/10* (2013.01); *G01N 1/28* (2013.01); *G01N 13/02* (2013.01); *G01N 2001/1031* (2013.01); *G01N 2013/0208* (2013.01)

(58) Field of Classification Search
CPC ........ G01N 33/2888; G01N 1/10; G01N 1/28; G01N 13/02; G01N 2001/1031; G01N 2013/0208; G01N 1/2813
See application file for complete search history.

(56) References Cited

U.S. PATENT DOCUMENTS

2005/0247137 A1* 11/2005 Nickerson ............ G01N 11/142
                                                                73/846

OTHER PUBLICATIONS

Zisman, W. A., Relation of the Equilibrium Contact Angle to Liquid and Solid Constitution, Fowkes; Contact Angle, Wettability, and Adhesion, Advances in Chemistry; American Chemical Society: Washington, DC, 1964. p. 1-51.

(Continued)

*Primary Examiner* — Herbert K Roberts
*Assistant Examiner* — Anthony W Megna Fuentes
(74) *Attorney, Agent, or Firm* — Edel Patents LLC; John B. Edel

(57) ABSTRACT

Methods of evaluating viscous compositions are disclosed. These methods may be used to evaluate volumetric properties of fluids including peanut butter. The methods may include preparing a surface for testing by leveling and flattening a viscous composition, placing a drop of a liquid on the flattened leveled surface, evaluating the observed contact angle between the drop and the surface, and then comparing the observed contact angle to a reference contact angle.

13 Claims, 17 Drawing Sheets

(56) References Cited

OTHER PUBLICATIONS

Final Report for NCHRP RRD 316: Using Surface Energy Measurements to Select Materials for Asphalt Pavement; Appendix D, Proposed Test Method to use a Sessile Drop Device to Determine Surface Energy Components of Asphalt Binders. (2007) National Academy of Sciences. ISBN 978-0-309-43174-3.

Orme et al. Apparent Contact Angles on Lubricant Impregnated Surfaces/SLIPS:From Superhydrophobicity to Electrowetting Langmuir 2019, 35, 4197-4204. Published Feb. 13, 2019.

* cited by examiner

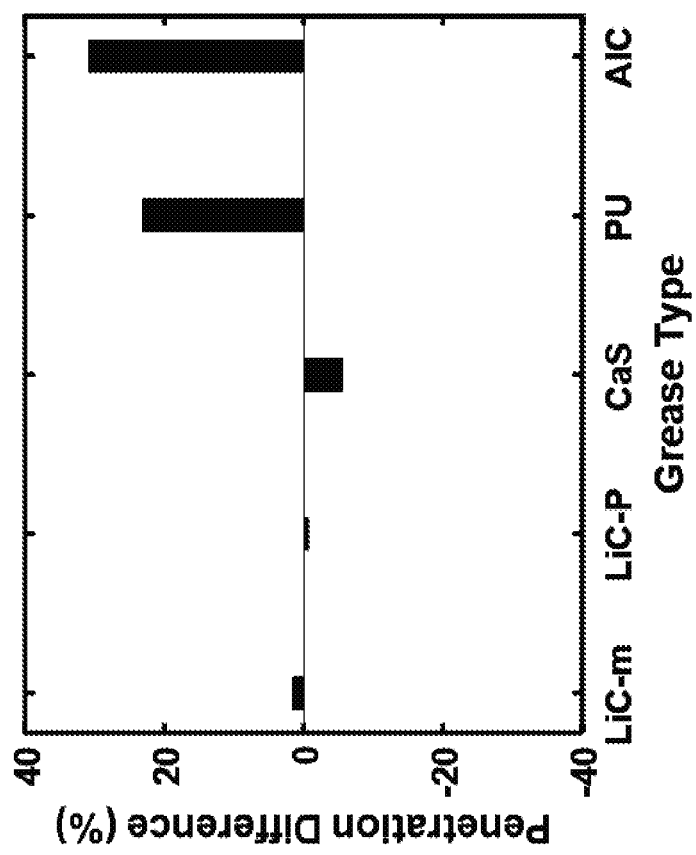
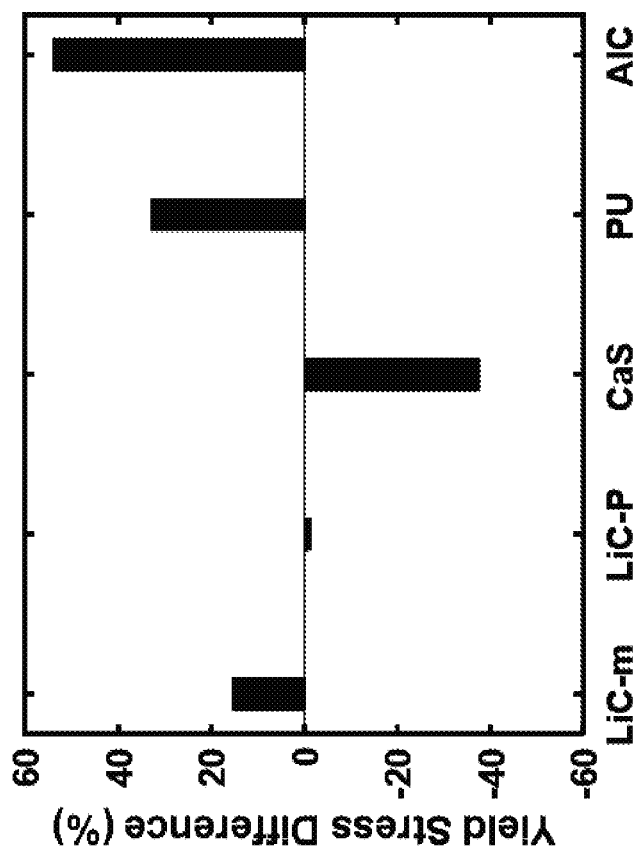
Fig. 15A
Fig. 15B

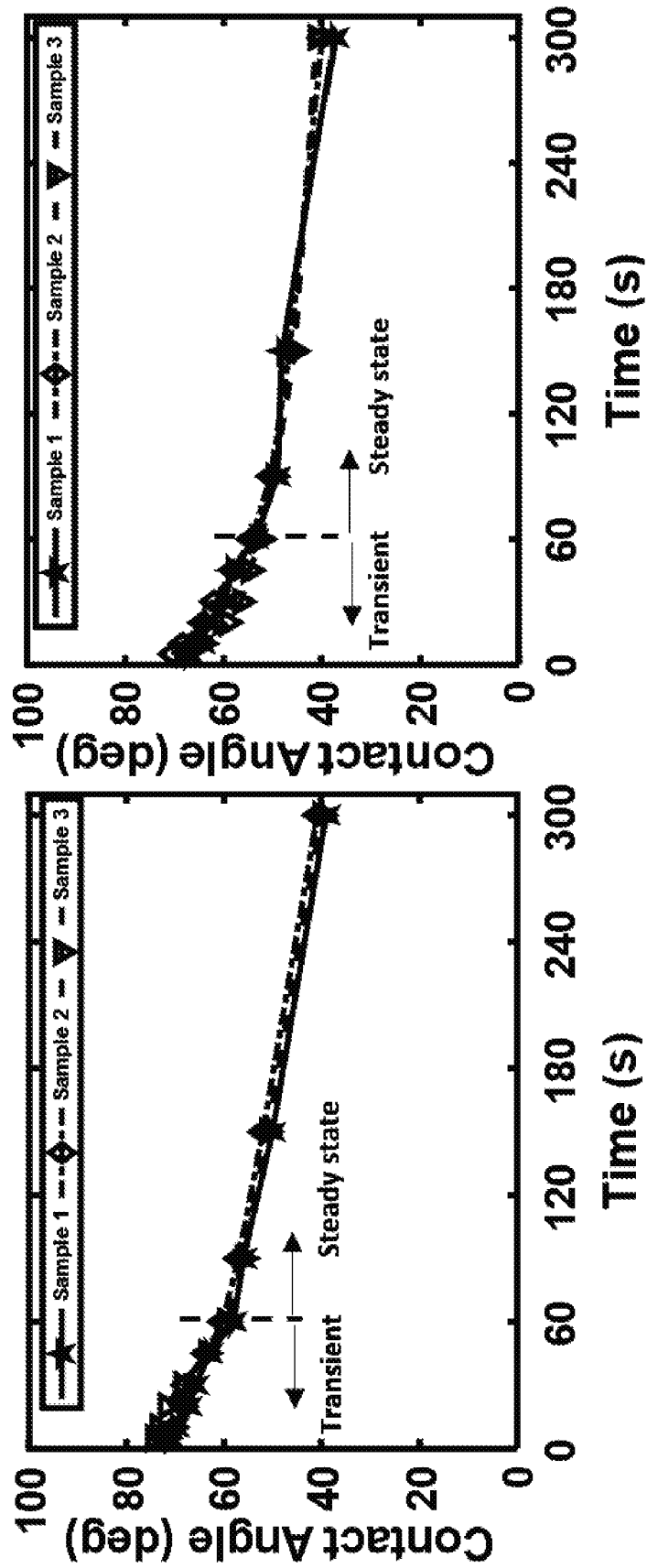

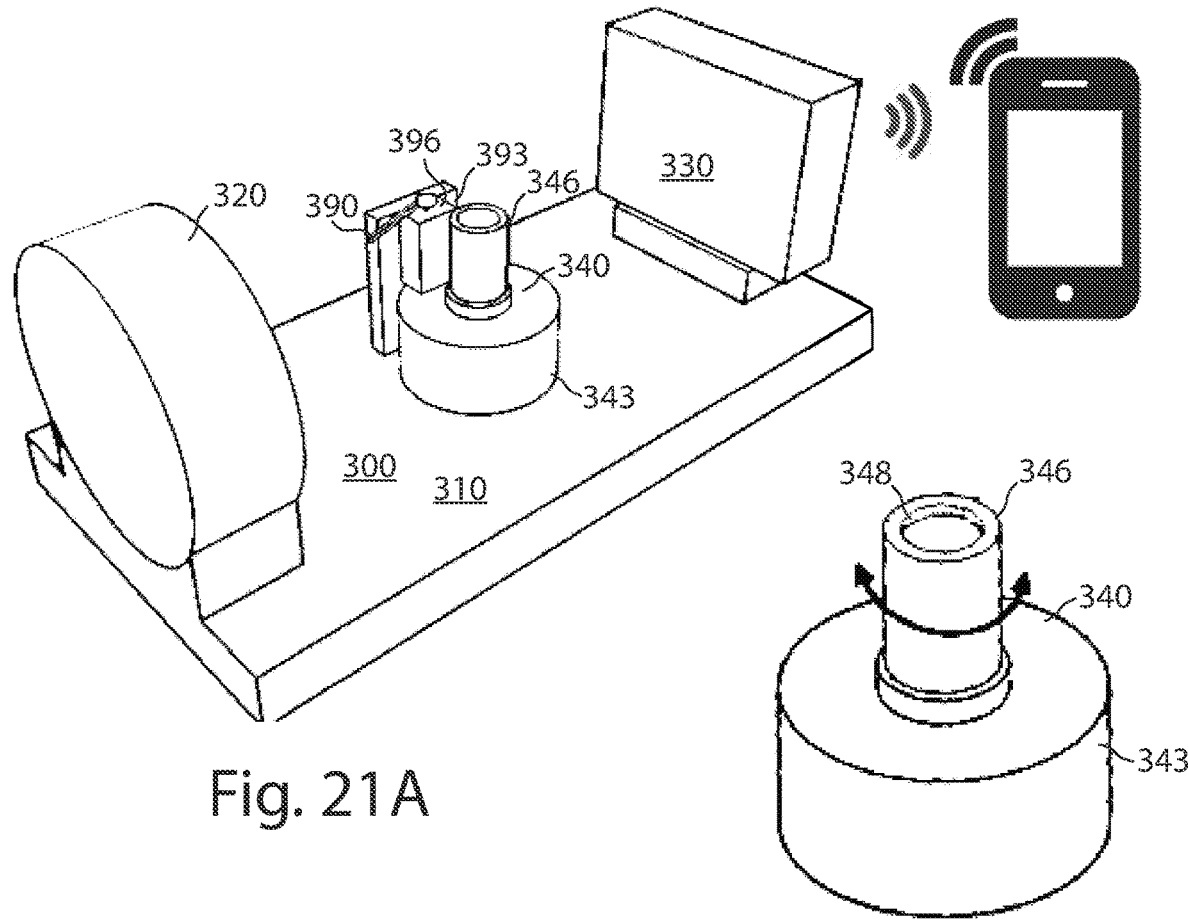
Fig. 21A
Fig. 21B
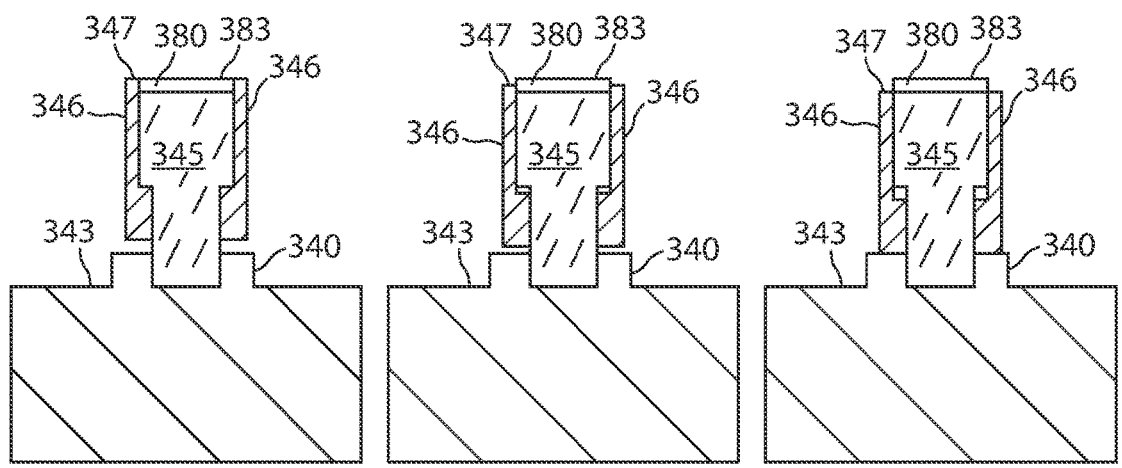
Fig. 20A      Fig. 20B      Fig. 20C

PEANUT BUTTER EVALUATION

Peanut butter evaluation techniques described herein may be used in characterizing the condition of peanut butter. Grease evaluation techniques described herein may be used in characterizing the condition of various greases. Certain grease evaluation techniques disclosed herein may indicate water contamination of grease. Certain grease evaluation techniques disclosed herein may indicate other forms of grease degradation.

BRIEF DESCRIPTION OF THE DRAWINGS

FIG. 15A depicts yield stress differences from water contamination.

FIG. 15B depicts penetration differences from water contamination.

FIG. 17A depicts contact angle values for PU greases without water.

FIG. 17B depicts contact angle values for PU greases with water.

FIG. 20A depicts a grease assembly with the collar extended.

FIG. 20B depicts a grease assembly with the collar partially retracted.

FIG. 20C depicts a grease assembly with the collar fully retracted.

FIG. 21A depicts a portable contact angle measuring device.

FIG. 21B depicts a grease handling assembly.

DETAILED DESCRIPTION

Example Set 1

Figure 1:
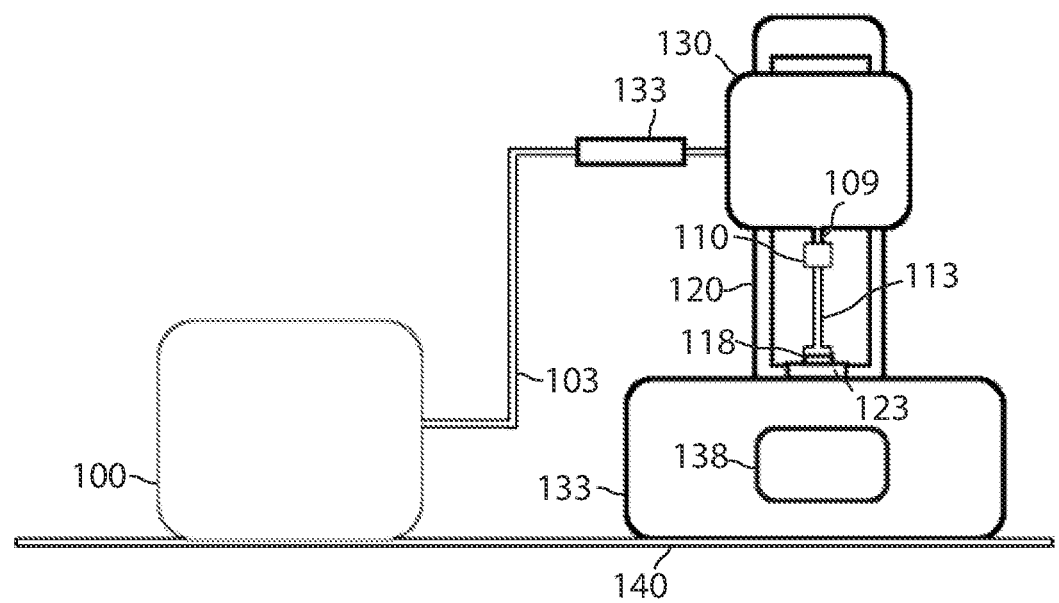
FIG. 1 depicts a rheometer for measuring the rheological properties of grease.

Many grease-lubricated machineries components operate in wet environments, making them susceptible to water contamination. The presence of a mere 1% water contamination in certain grease may reduce the life of a bearing by 90%. Methods described herein may evaluate the capability of grease to repel water along with other potential indicators relating to the performance of grease. Methods described herein utilize the contact angle of a water droplet on a grease surface to quantify grease water resistance. The measured contact angle may be correlated to the hydrophobic nature grease and the extent of an individual sample's hydrophobic nature. A variety of commercially available greases were tested. The efficacy of contact angle results was established by measuring the change in the yield stress values obtained using a rheometer. Contact angle testing as described herein may be used to distinguish various greases as having differing strengths of water repellent properties.

Grease is a highly complex lubricant composed of thickeners, additives, and base oils. Compared to lubricating oil, grease provides good sealing properties, requires less maintenance, and can even operate in a solid-contaminated environment. However, as a water absorbing and non-Newtonian semi-solid the behavior of grease in contact with water is dynamic and presents measurement challenges.

The working life of grease may be profoundly affected by contaminants, such as water, which tends to modify their chemical structure and degrade their rheological properties, which, in turn, negatively affects the performance of the machinery components. Some greases become firmer with water, leading to a reduced ability to replenish the contacts, and resulting in excessive power consumption.

Water contamination may trigger several structural and chemical mechanisms leading to premature failure of grease. Appropriate grease selection can prolong the safe working operation of vital components/machinery.

Some calcium/lithium-based soaps thicken in response to water contamination, while others tend to become thin. This trend makes it difficult for the practitioner to select the best water repellant candidate between two greases having the same magnitude of change where one thickens while other thins. The rheological approach fails to assess the water-repellant properties in a single platform. Further, the quantity of sample required for rheological testing makes this approach difficult to use in the assessment of used grease samples collected from process operations.

The water-repelling nature of grease may be measured by evaluating the contact angle of a water droplet on a grease surface. A grease having good water-repellent properties will have poor wettability, appear hydrophobic in nature, and exhibit a large contact angle. By the same token, a grease attracted to water tends to have good wettability properties, appear hydrophilic in nature, and exhibits a smaller contact angle. Methods described herein provide a quick tool for researchers and manufacturers of semi-solid substances such as peanut butter looking to optimize hydrophobic or hydrophilic characteristics while screening different combinations of additive chemistries and thickeners.

Methods described herein evaluate the response of grease to water. The water resistance property of grease is measured, and that measurement enables a practitioner to formulate the water resistance property of a grease during its development stage to achieve the desired properties.

To validate the hypothesis, as a first step, the performance of the grease in the presence of water was determined by measuring the different rheological properties such as yield stress using a rheometer. In this approach, the change in rheological properties between the pristine and water contaminated greases is determined to estimate the performance of the grease in the presence of water. The samples were contaminated with water by the static absorption method, i.e., grease is immersed in water for a definite duration, and the samples are tested after draining the water. Lastly, the contact angle values of the water droplets were measured on the pristine grease surface using a drop shape analyzer. Obtained values of rheological properties and contact angle values are then compared to establish the efficacy of the proposed approach.

Experiments were performed on seven different types of commercially available NLGI grade 2 greases. The details of the greases used are provided in Table 1.

TABLE 1

Grease designation with thickener and base oil types

| Grease label | Thickener types | Base oil type |
|---|---|---|
| LiC_m | Lithium complex | Mineral oil |
| LiC_P | Lithium complex | Poly-alpha-olefin oil |
| CaS | Calcium sulfonate | Mineral oil |
| PU | Poly-urea | Mineral oil |
| Si | Silicone | Synthetic oil |
| AlC | Aluminum complex | Mineral oil |
| WLi | White lithium | Mineral oil |

Mixing grease with water through mechanical shearing action leads to degradation of grease. Grease samples were contaminated in a static-type condition using the following procedure. First, 5 g of a grease sample is immersed in 50 g of water at room temperature (25° C.) for 24 hrs. After 24 hours, water was drained out, and the samples were tested in a rheometer as described below.

The rheological properties of the grease were studied using the Anton Paar MCR 301 rheometer depicted in FIG. 1.

This rheometer was equipped with a rotating plate with a diameter of ~25 mm connected to the driving motor using a coupling. The air supply to the motor was provided using an air compressor. Referring to FIG. 1 of the drawings, the rheometer set up on table 140 includes an air compressor 100 which supplies driving motor 130 through air hose 103 and air filter 133. Motor shaft 109 is connected to Plate 113 by coupling 110. Plate 113 works grease 118 against stationary surface 123. The instrument includes a controller with a gap motor 133 and digital display 138. The specifications of the rheometer were as follows: torque 0.1 mN·m-200 mN·m with a resolution of 0.001 pN·m and accuracy of 0.2 pN·m, applied load of range 0.005 N to 50 N with a resolution of 0.002 N, accuracy±0.03 N, the rotational speed of the rheometer was $10^{-6}$ rpm-3000 rpm. The temperature of the rheometer can be controlled between in the range of −40° C. up to 200° C. with an error of ±0.1° C. There are several rheological properties, e.g., yield stress, through which the grease performance can be evaluated.

Figure 2:
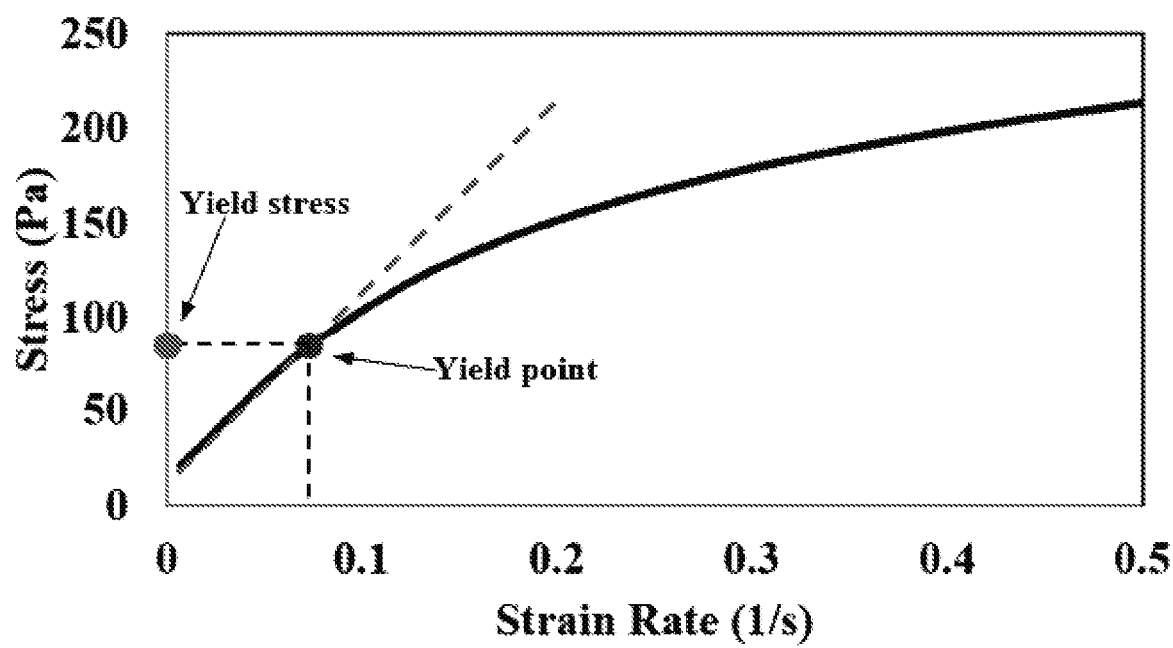
FIG. 2 depicts stress-strain plot.

The yield stress of grease is defined as the point on the stress versus strain curve where the linear behavior of the grease deviates from the experimental data by a prescribed amount or it is taken at the stress level at which the Maxwell model is no longer linear. FIG. 2 depicts the stress-strain plot indicating the yield point.

The stress-strain plot is obtained by oscillating the plate of the rheometer at a fixed frequency of 1 Hz while maintaining the grease sample thickness of 1 mm and sweeping the amplitude of the shear rate from 0.01 to 1 s$^{-1}$. To determine the point at which a deviation occurs in the stress-strain plot, the procedure proposed by Cyriac et al. is adopted. See: F. Cyriac, Lugt P. M., Bosman R. On a new method to determine the yield stress in lubricating grease. Tribology Transactions, 58(6) 1021-1030, 2015.

According to this procedure, the yield stress is the point where the coefficient of determination (R$^2$) between the third-order polynomial fit of the experimental values and linear fit, is greater than 99.5%.

$$\tau_{diff}\% = \frac{(\tau_{pr} - \tau_{con})}{\tau_{pr}} \times 100 \tag{1}$$

where $\tau_{pr}$ and $\tau_{con}$ are the yield stresses obtained for the pristine and water contaminated greases, respectively.

Figure 3:
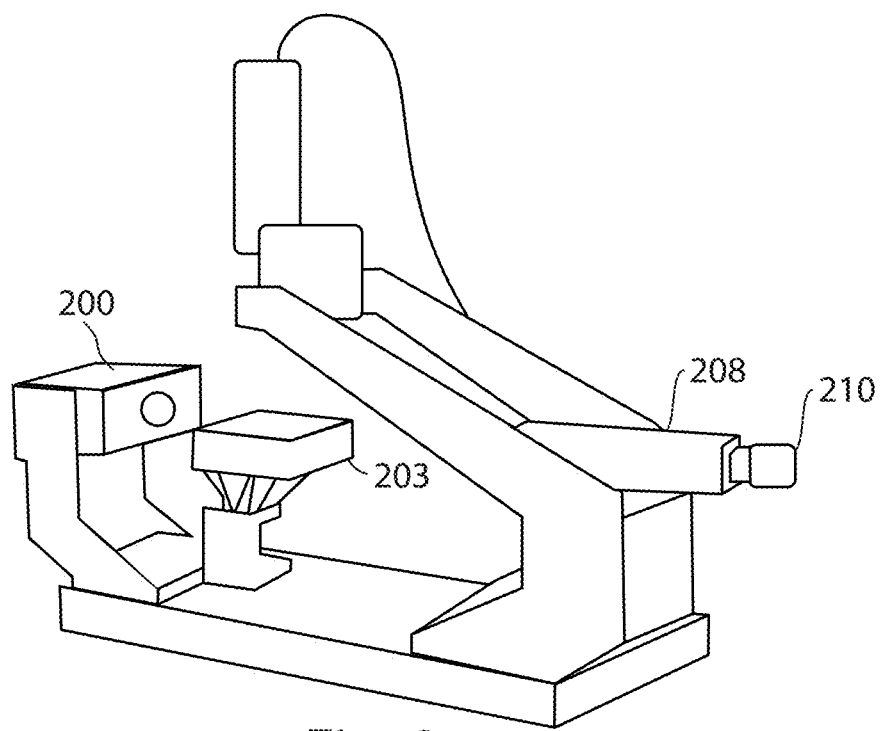
FIG. 3 depicts a drop shape analyzer.

To measure the contact angle of a water droplet on the grease surface, a drop shape analyzer shown in FIG. 3 was employed. In FIG. 3, monochromatic light source 200 shines over adjustable sample platform 203 and camera 210 captures the resulting light through lens 208. Samples are positioned atop adjustable sample platform 203. In this setup, grease samples to be tested are placed on the adjustable sample stage and the height of the stage is set to the level of the lens using an adjustable screw. A water droplet is placed on the grease surface using a 10 μl syringe, and the focus and zoom of the droplet are adjusted using the adjustable lens (Thorlabs AC254-075-A-ML Lens). The image of the droplet is captured using the camera (IDS UI-5480CP-M-GL GigE camera) attached to it. The monochromatic blue light provides a clear black image of the droplet. From the captured image, the contact angle θ is calculated by the built-in software.

Software from the drop shape analyzer failed to automatically determine the base line for the grease which required a manual fixing of the base line and the point of contact for the grease. The use of the mold used to establish the grease surface likely led to the challenges with the use of the equipment. A more automated sequence and a removable and/or retractable mold may allow for consistent automated identification of the base line and the point of contact for the grease.

Figure 4A:
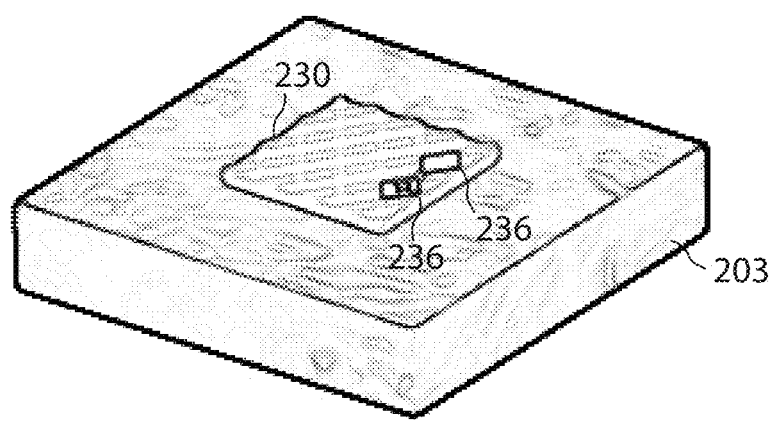
FIG. 4A depicts an adjustable sample platform supporting a grease mold.
Figure 4B:
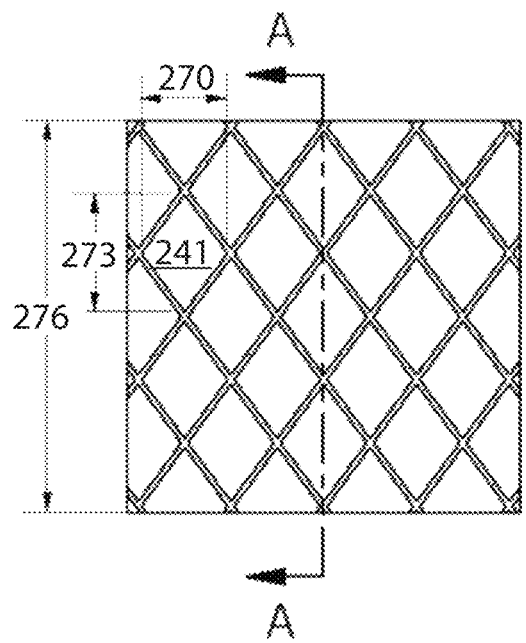
FIG. 4B depicts a top view of a grease mold.
Figure 4C:
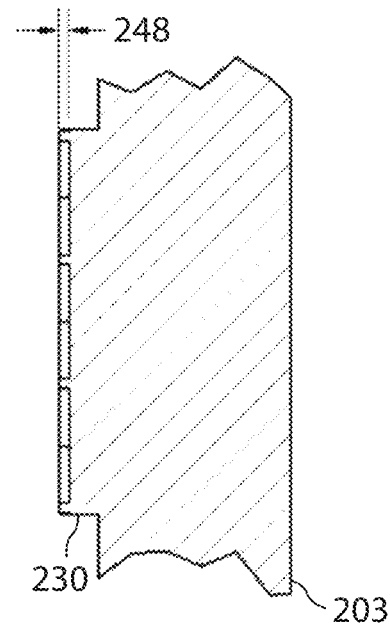
FIG. 4C depicts a cross section of FIG. 4B.
Figure 4D:
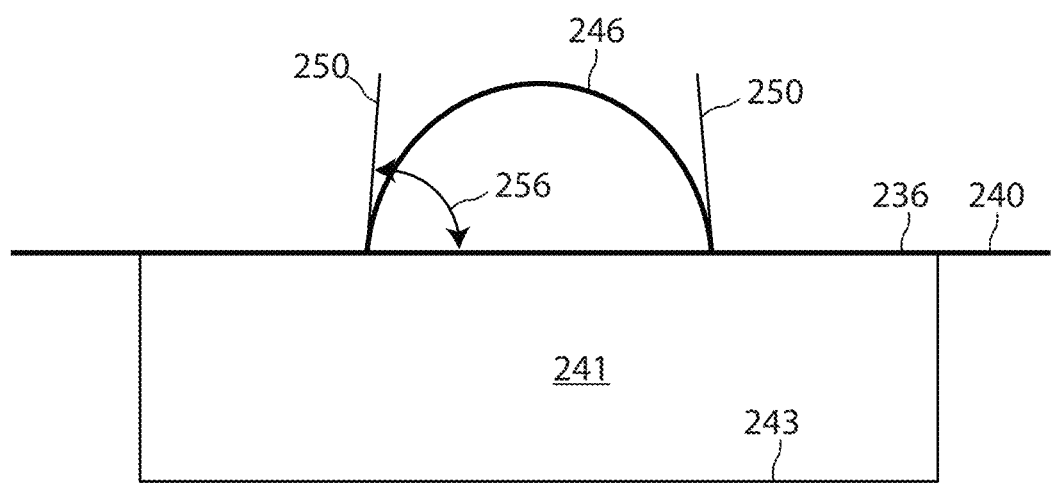
FIG. 4D depicts a partial cross-section of FIG. 4B.

To achieve repetitive results, it is helpful to have an unvarying thickness of the grease and uniform surface during every test. For this purpose, a special mold made of polymer, consisting of several rhombus-shaped slots, is employed, and a systematic procedure is followed in all measurements. FIG. 4A depicts adjustable sample platform 203 supporting grease mold 230 on which grease surface is 236 have been established in perspective view. FIG. 4B is a top view of grease mold 230 depicting dimensional characteristics for slot width 270, which may be 10 mm; slot height 273, which may be 15 mm; and mold width 276, which may be 50 mm. FIG. 4C is a cross-section of FIG. 4B depicting slot 241; slot depth 248; which may be 5 mm, grease mold 230; and adjustable sample platform 203. FIG. 4D is a partial cross section of FIG. 4B depicting grease surface 236, mold top surface 240, slot 241, mold slot bottom surface 243, water droplet 246, contact angle droplet tangent lines 250 and contact angle 256 which may be represented by the symbol theta.

The schematic representation of the mold in perspective view with grease in the slots and water droplet on the grease surface is shown in FIGS. 4A and 4D. The dimensions of the rhombus slots are as follows: length—15 mm, breadth—10 mm and thickness—0.5 mm as depicted in FIGS. 4B and 4C and described above. From the dimensions of the polymer mold, it can be inferred that this mold requires a small quantity of grease for testing. This allows the practitioner to perform several tests on a degraded grease sample extracted, for example, from a bearing in the field. Further, the multiple slots in the mold reduce the sample preparation as well as testing time, providing a constant grease height for all tests. The constant height of the samples allows easy identification of the base of the water droplet and for easy detection of the droplet edges for accurate measurement of contact angle. In an alternate embodiment, the grease could be placed on a glass slide with equivalent guides designed to control the uniformity of the thickness of the grease and make the top surface of the grease parallel to the top surface of the slide.

To achieve a grease surface of the same height of the mold surface as well as for attaining a uniform surface finish of the grease samples, three steps may be followed. First the grease sample may be collected from the grease cup or other sampling vessel using a spatula and applied on top of the slots of the mold. Second, using a glass slide, the excess grease may be wiped off in a first direction which may be in alignment with the longest dimension of an individual slot 241. Third, the wiping with the glass slide may be done again along mold top surface 240 in a direction perpendicular to previous wipe. The slot containing the grease to be tested is kept in front of the camera and a 5 µl water drop is placed on the grease surface. The droplet is captured using the camera and analyzed using the software.

Figure 6:
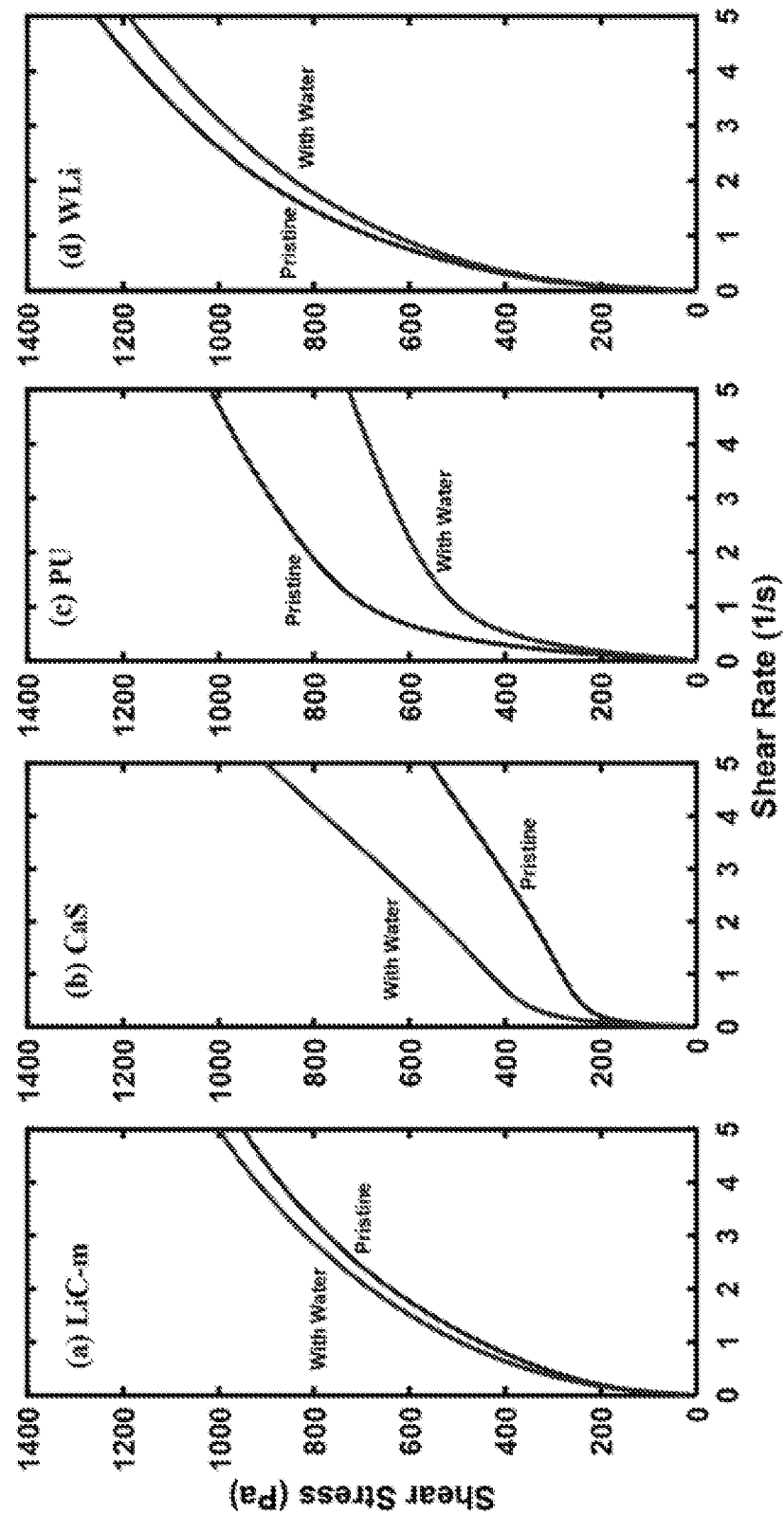
FIG. 6 depicts stress strain curves for various types of grease.

The yield stress values for the pristine and water-contaminated LiC-m, LiC—P, CaS, PU, Si, AlC, and WLi greases were determined from the shear stress-strain values. The plots of shear stress and strain for LiC-m, CaS, PU, and WLi greases are shown in FIG. 6. To avoid redundancy, the values for other types of greases are not plotted. FIG. 6 reveals that the values of shear stress for pristine LiC-m and CaS greases are lower than water contaminated greases while suggesting an opposite trend for PU and WLi greases.

Figure 5:
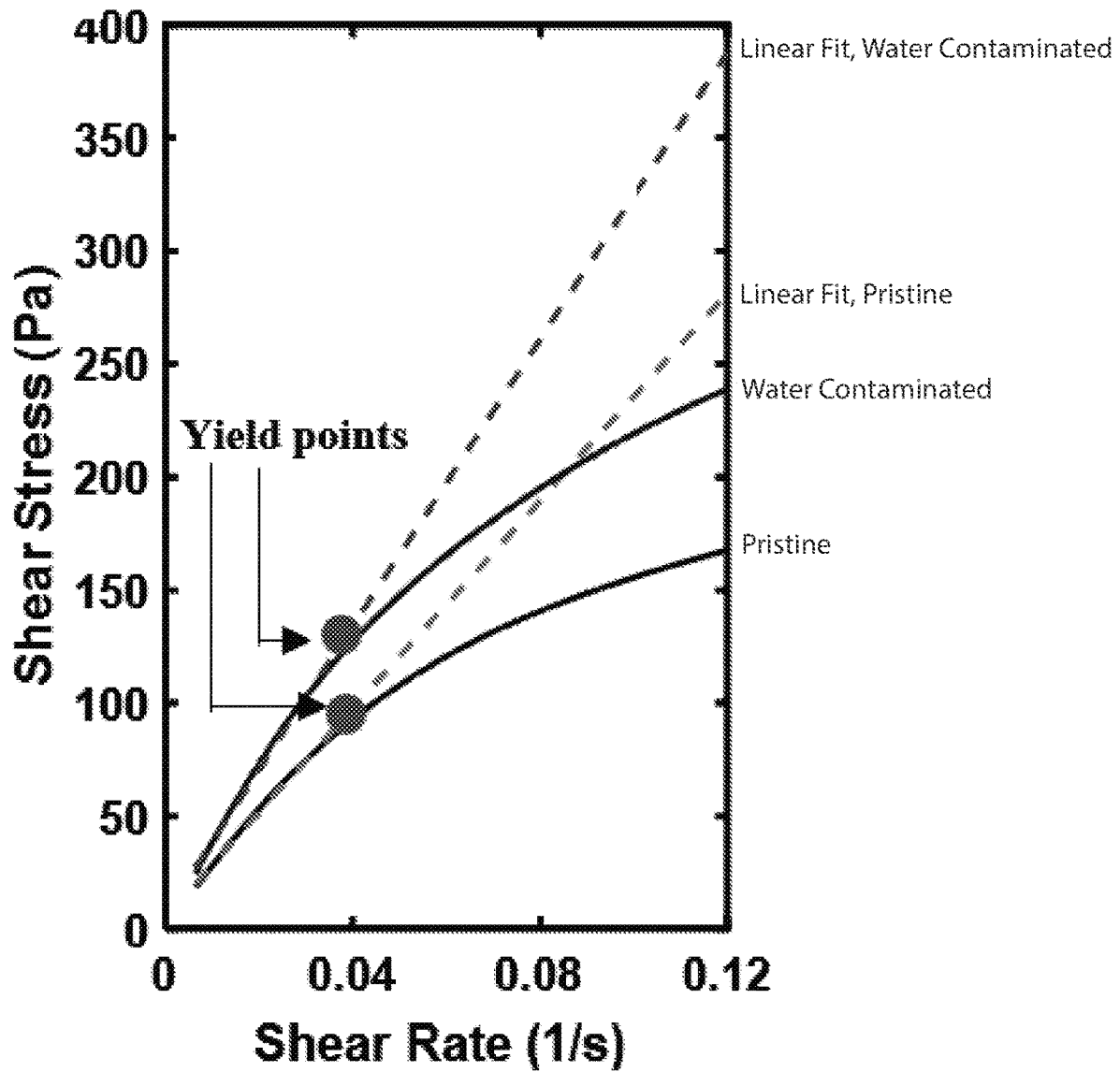
FIG. 5 shows stress-strain curves for contaminated and uncontaminated grease.

From the plotted shear stress vs. strain values, and using the linear fit function in Matlab, a numerical computing environment, the yield stress values were determined for $R^2 > 99.5\%$. Experimentally determined shear stress-strain values and their linear fits for both the pristine and water contaminated CaS grease are shown in FIG. 5. The percentage change in the yield stress values determined using Eq. (1) for all the greases are provided in FIG. 7. From this figure it can be observed that the variation in the yield stress values for all the greases follow the same trend. For LiC-m and CaS greases, the change in yield stress values is negative, indicating that these greases thickened with water contamination. For other types of greases, the yield stress values decreased, or, in other words, the consistency reduced with water contamination.

Figure 8:
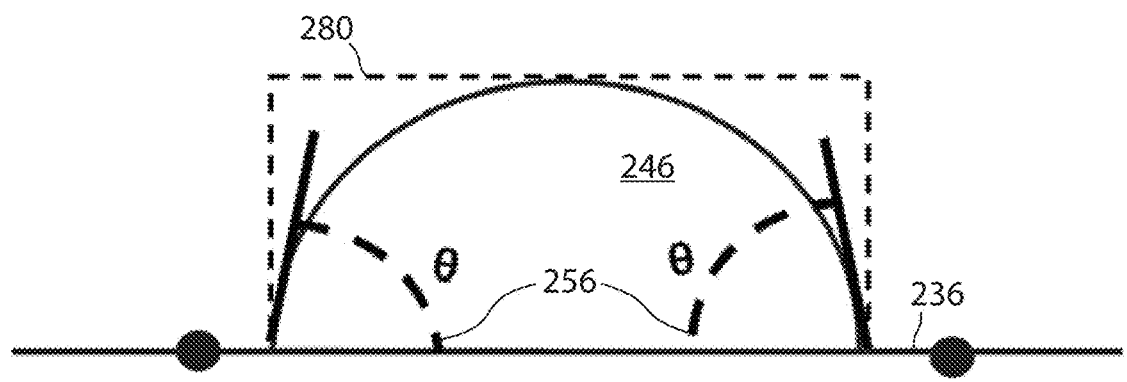
FIG. 8 depicts contact angle relative to a drop on a surface.

Grease is a semi-solid substance with a complex structure. When a water droplet is placed on a grease surface, it tends to spread and/or gets absorbed by the grease. Therefore, the size of the droplet and the contact angle values change with time. To address these issues, a video of the droplet was recorded at 3 frames/s and the images at different intervals are analyzed for the contact angle. The contact angle values for the droplet are determined using the length/breadth approach, provided in the instrument's software. A drop shape analyzer model no. DSA25E from KRÜSS GmbH Wissenschaftliche Laborgeräte was used in the experiment. In this approach, partially depicted in FIG. 8, the length and breadth of a rectangle 280 positioned atop grease surface 236 are manually adjusted to the edges and peak point of the water droplet 246 for the calculation of contact angle 256. Further, this establishes the baseline for calculating the contact angle. To gain more confidence on the obtained results, the contact angle values are determined for two droplets on opposite edges of slot 241. This technique further reduces the grease requirements of the test. For each type of grease, a minimum of nine sets of readings were taken.

Figure 9:
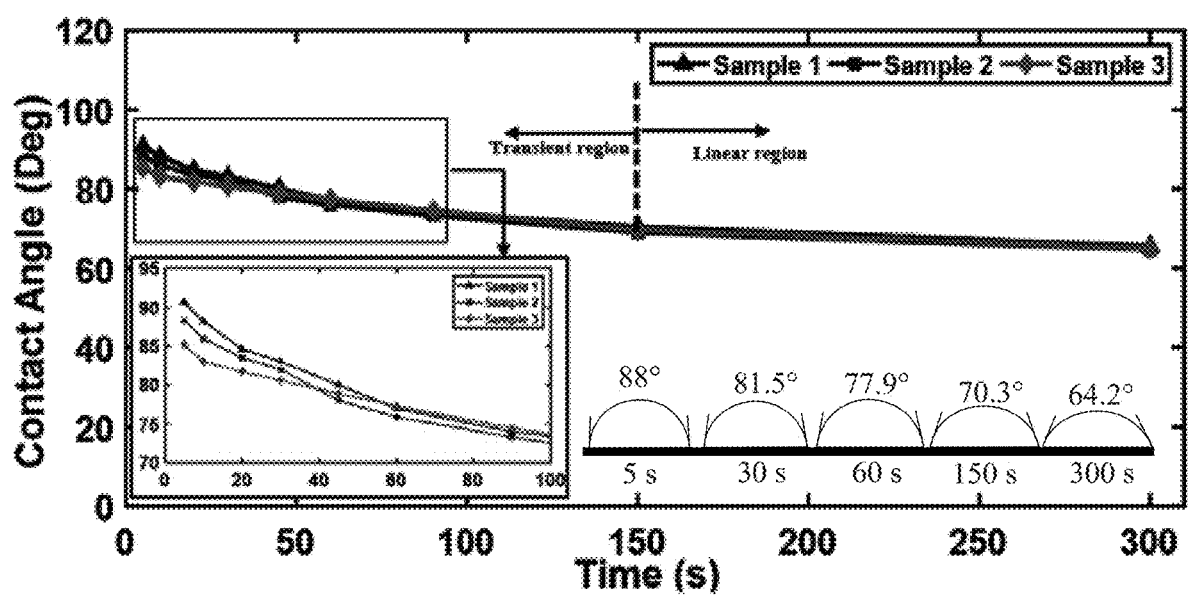
FIG. 9 depicts time-dependent contact angle measurements on pristine LiC-m grease.

Three sets of measurements from nine series of experiments on a pristine LiC-m grease are shown in FIG. 9. This figure also provides the captured water droplet images at 5, 30, 60, 150 and 300 s. Referring to this figure it can be observed that the contact angle varies with time, and that the values decrease non-linearly for the first 150 s, after which the rate of change becomes small and linear. It is interesting to note that the variation in the contact angle values among the samples are somewhat scattered during the first 45 s of the process but become invariant and "stabilize" thereafter.

Figures 10A, 10B, 10C:
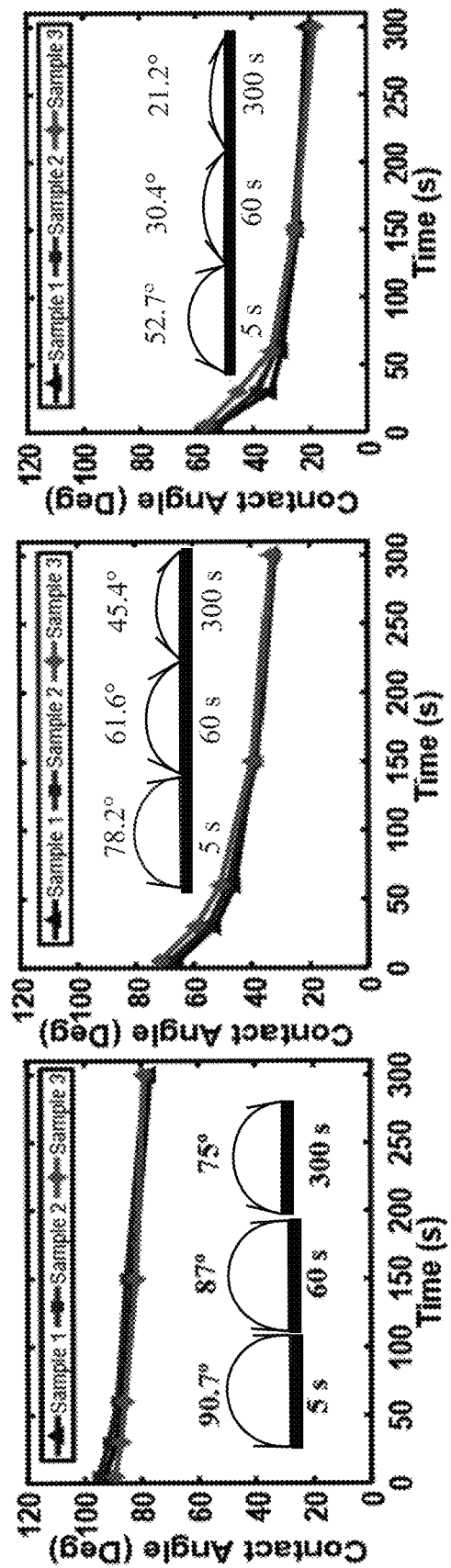
FIG. 10A a depicts time-dependent contact angle values for pristine CaS grease.
FIG. 10B a depicts time-dependent contact angle values for pristine PU grease.
FIG. 10C a depicts time-dependent contact angle values for pristine WLi grease.

Similarly, the contact angle values and captured droplet images for PU, CaS, and WLi greases are shown in FIG. 10A-10C. The progression of contact angles is similar in all cases, exhibiting a nonlinear transient behavior that stabilizes after 150 seconds. Certain methods for establishing the contact angle may including a measurement delay in which the contact angle becomes more stable. The measurement delay may be at least 10 s or at least 30 s.

Now, referring to the values of contact angle plotted in FIGS. 9 and 10, the following general observations can be made. (i) contact angle values reduce with time, (ii) the variation in the contact angle values among different samples tend to be somewhat scattered until 60 s but become invariant thereafter (iii) the values decreased non-linearly until 150 s and, subsequently, the values stabilize and drop linearly at a relatively small rate of change. Evaluation of contact after 60 s can be considered to provide adequate information for practical purposes. The average values of contact angle for all the nine samples of the greases at 60 s are determined and plotted in FIG. 11.

The level of degradation of the grease with water contamination is determined from the percentage change in the yield stress properties $\tau_{diff}\%$ between the pristine and the water contaminated grease. The value of $\tau_{diff}\%$ is determined using Eq. (1).

Figure 7:
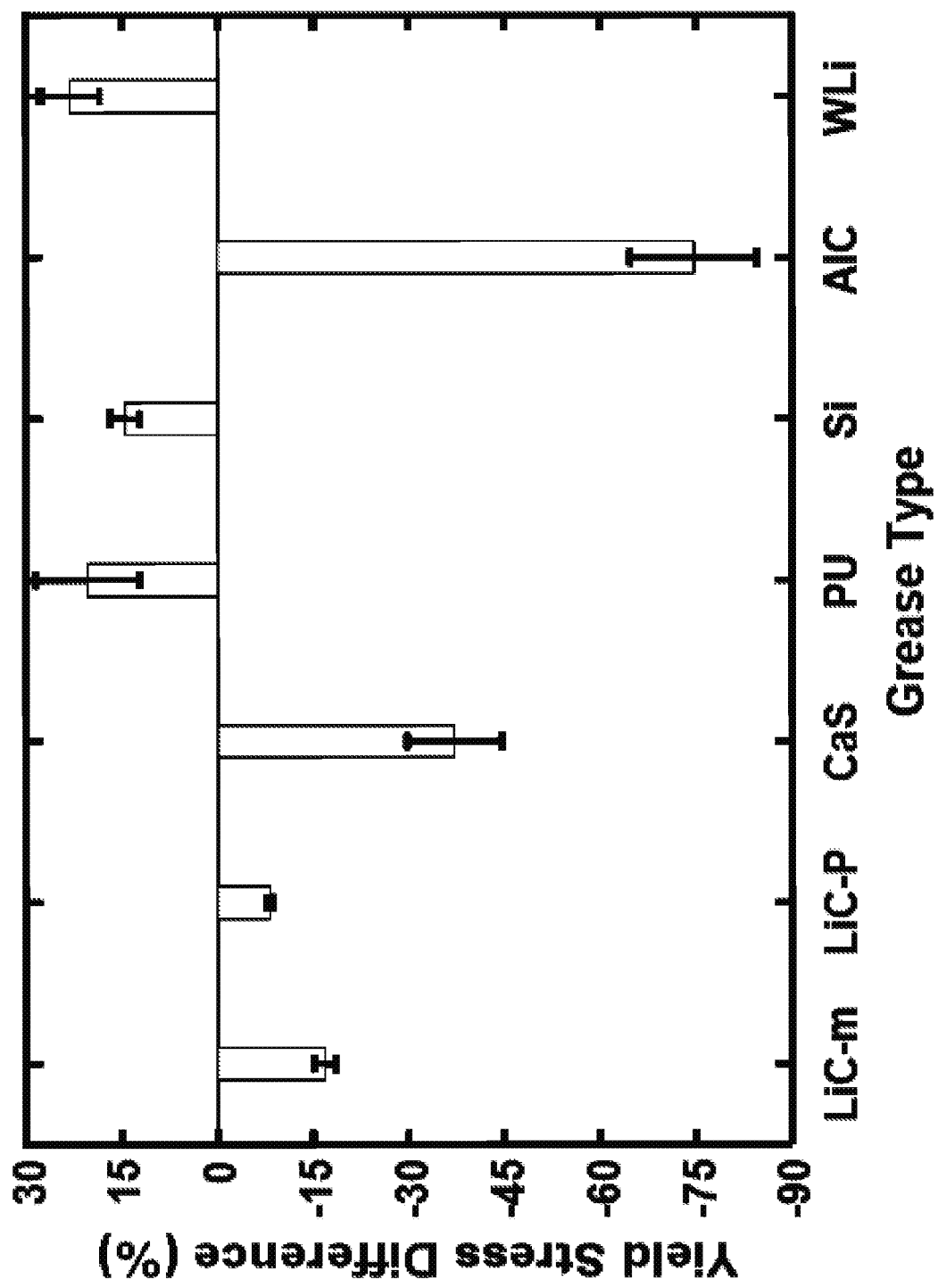
FIG. 7 depicts yield stress variations relative to water contamination.

The change in the yield stress values with water contamination are provided in FIG. 7. Yield stress may either increase or decrease due to water contamination. Note that the change in the yield stress values for LiC-m, LiC—P, CaS and AlC greases are negative, while for PU, Si and WLi they are positive. The drastic positive and negative values in the rheological properties make the interpretation of grease resistance to water difficult for the practitioners. Specifically, among the PU, Si and WLi greases, it is clear that Si grease will exhibit better water-resistant characteristics, while the WLi grease will not have the same water-resistant characteristics in the presence of water. However, it is not clear whether the test performance of the Si grease is better than LiC-m, LiC—P, CaS, and AlC greases. Therefore, an alternative approach to assess the grease's performance in water contamination is necessary.

Only a minute quantity of grease is needed for optical testing. For the circular cross-section plate of 25 mm diameter and for 1 mm grease thickness, the volume of grease used in the rheometer is ~490 mm$^3$. On the other hand, the volume of grease used in the rhombus slot is determined to be 75 mm$^3$, using roughly on sixth of the grease vs. the rheometer.

Figure 11:
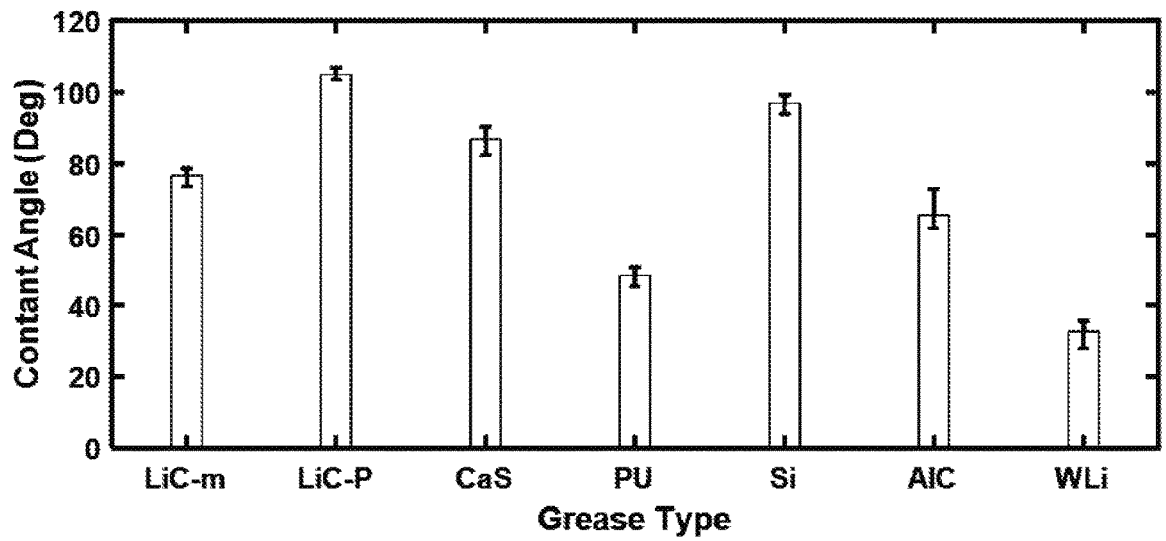
FIG. 11 depicts average contact angle values for samples as measured at 60 seconds.

The average values of contact angle for all the considered samples of the greases at 60 s is plotted in FIG. 11. This figure suggests that the contact angle values for LiC—P and Si greases are greater than 90°, and for CaS grease it is approximately equal to 90°. This indicates that the water droplet remains on the grease surface as free water for a relatively long time. In the case of LiC-m grease the value of θ<90°, and for PU, AlC and WLi greases θ<<90°, indicating the grease either spreads or gets absorbed faster into the grease. The contact angle results indicate the order of water repellant properties are:

LiC—P>Si>CaS>LiC-m>AlC>PU>WLi

Now, for better comparison, the values of the percentage difference of yield point and contact angle values obtained are provided in Table 2. In this table, the first three greases illustrated positive change, while the last four values showed a negative change in the yield points. Further, it can be observed that both approaches predicted the same order of water-repelling properties for the greases having a positive change of yield point, i.e., Si>PU>WLi. However, in the case of a negative change of yield point, the order predicted for LiC-m and CaS greases are opposite. Therefore, it can be concluded that the order predicted by the contact angle approach is correct compared to the rheological approach.

TABLE 2

Comparison of change in yield point difference percentage and contact angle

| Grease Types | Yield point difference (%) | Contact angle (°) |
|---|---|---|
| Si | 14.42 | 96.8 |
| PU | 20.3 | 48.23 |
| WLi | 23.06 | 32.5 |
| LiC-P | −8.2 | 104.95 |
| LiC-m | −16.81 | 76.58 |
| CaS | −37.13 | 86.7 |
| AlC | −74.63 | 65.58 |

Figure 12:
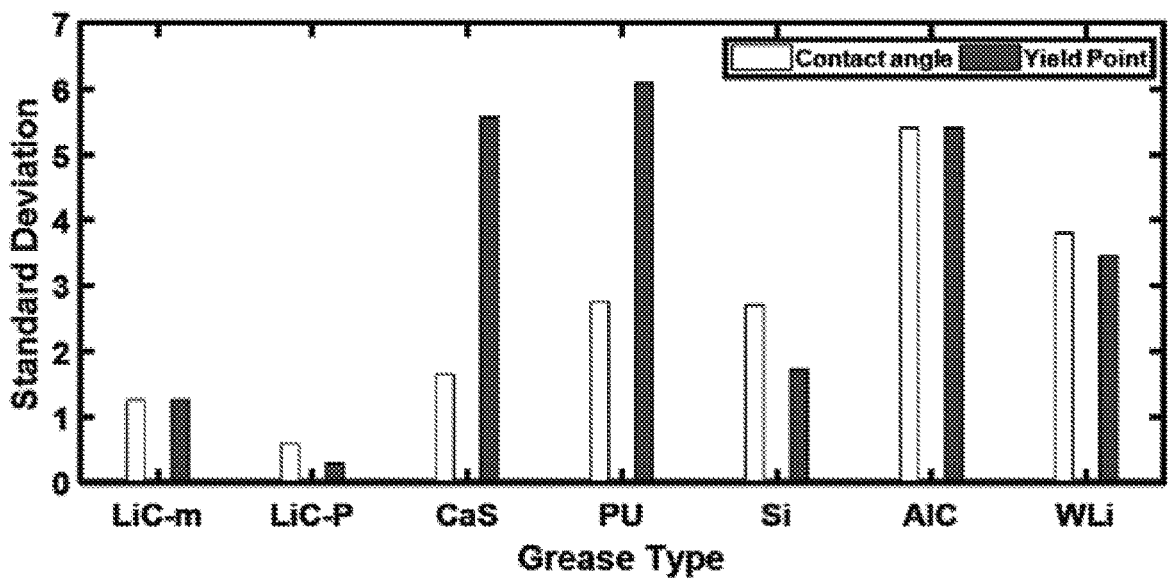
FIG. 12 depicts yield point and contact angle values.

To establish the precision of the proposed approach, the standard deviation in the values of percentage difference of yield point and contact angle values are determined for different greases and presented in FIG. 12. From this figure it can be observed that the values of standard deviation determined using both approaches are almost the same except for CaS and PU greases. In case of CaS and PU greases, the values of standard deviation determined for rheological method is higher than the contact angle approach. Therefore, it can be concluded that the proposed contact angle approach provides equivalent or better precision than rheological approach.

From the above discussion it can be concluded that the contact angle approach can quantitatively determine the water resistance properties of the grease.

An attempt is made to characterize the water repulsion properties of seven commercially available greases (LiC-m, LiC—P, CaS, PU, Si, AlC and WLi) by measuring their rheological properties such as yield stress and comparing these data with a new method that measures the contact angle of a water droplet on the greases' surface. For determining the water-resistance properties using the rheological approach, shear stress-strain plot values are obtained for pristine and water contaminated greases. Obtained results indicate that for LiC-m, LiC—P, CaS and AlC greases, the consistency of the grease increased with the inclusion of water, while for the other three greases: Pu, Si, and WLi the consistency was reduced. Therefore, it was concluded that the yield point analysis approach is a relative approach and not capable of providing clear differentiation in water repulsion performance in a single test. In contrast, it was established that the contact angle approach, which requires six-fold less volume of grease compared to the rheological approach, will allow the practitioner to test multiple numbers of times. Further, the proposed approach can provide a comparative order of water-repelling properties of all the greases in a single platform. The values of contact angle θ observed for different greases are: LiC—P, and Si>90°, CaS θ~90°, LiC-m<90°, and PU, AlC and WLi θ<<90°. For this limited study, the greases with θ≥90° can retain water on the grease surface as free water for a relatively long time while for θ<<90°, the water either spreads or gets absorbed faster into the grease. The order of the grease having water repellant properties are: LiC—P>Si>CaS>LiC-m>AlC>PU>WLi. The order of water-repelling properties predicted using the contact angle approach is more accurate than the rheological approach and, additionally, the standard deviation values predicted using the proposed contact angle approach either provided equivalent or better precision than the rheological approach.

Example Set 2

Measurements were taken to determine the water repelling nature of grease by measuring the contact angle of a water droplet on a grease surface. Grease having good water-repellent properties may have poor wettability, appear hydrophobic in nature, and exhibit a large contact angle. By the same token, a grease attracted to water shall have good wettability properties, appear hydrophilic in nature, and exhibit a smaller contact angle. Therefore, when a grease is contaminated with water, grease becomes more hydrophilic and consequently the contact angle reduces. Five different greases are considered and contaminated with water. Grease is contaminated with 60% of water by shearing mechanically in a modified grease worker for 10000 strokes. During the mixing of grease with water, grease degrades due to shearing and water contamination. The experiment was performed with and without water and the change in properties was determined to identify the performance of grease in the presence of water.

As a first step, the performance of the water contaminated grease is determined by measuring the rheological properties (yield stress and penetration) using a rheometer. The performance is determined by measuring the difference in the rheological properties of greases sheared for 10000 strokes in the absence and presence of water. Similarly, the contact angle values of the water droplets are measured on both grease surface sheared under both conditions, using a drop shape analyzer. The results obtained for rheological properties and contact angle values are compared to establish the efficacy of the proposed approach.

Five types of grease samples from the commercially purchased grease cartridges were tested. These greases are commercially advertised as having good washout/marine grade greases. The details of greases used are provided in Table 3. For some types of grease, the base oil was observed to be settling with time therefore, grease from the cartridge is transferred into a bigger container and mixed well before considering for testing.

TABLE 3

Grease designation with thickener and base oil types

| Grease label | Thickener types | Base oil type | Color |
|---|---|---|---|
| LiC_m | Lithium complex | Mineral oil | Blue |
| LiC_P | Lithium complex | Poly-alpha-olefin oil | Pink |
| CaS | Calcium sulfonate | Mineral oil | Green |
| PU | Poly-urea | Mineral oil | Blue |
| AlC | Aluminum complex | White mineral oil | Green |

The mixing of water in grease is carried out in the modified grease worker rig. This rig contains a 2 hp gear reduction motor, grease cup, plungers, connecting rod, cam on drive unit and a load cell. The cam on drive unit converts the rotary motion of the motor to linear-reciprocating motion. The cup is made of plexiglass with the internal diameter of 40 mm and depth of 50 mm. The plunger is a metal disk of 38 mm diameter, 5 mm thick and contains eight 8 mm radial holes. The number of strokes is counted using an electric counter. The shearing action is induced in grease by reciprocating the plunger inside the cup and forcing grease to pass through the holes in the plunger.

Grease samples of 10 g mixed with water in plexiglass cup of grease worker at 1 s$^{-1}$ shear rate at room temperature (25° C.). Several experiments are performed for different number of strokes and percentage of water for finding the uniform mixing of grease and water, by visual inspection of color distribution of grease in plexiglass. For most greases, the color of grease became milky color from their original color. The color distribution of two greases: LiC-m and LiC—P after 1000 strokes showed lightening including some inconsistencies in the degree of lightening. In each cases the uniformity in color was observed after 10,000 strokes and further, it was observed that by the end of 10,000 strokes, the maximum percentage of water consumed by all greases was 50% of the original dry grease weight. In other words, adding water amounting to at least 50% of the dry grease weight would fully contaminate the whole grease in the container. Therefore, it was decided to add 60% water to the grease. Measuring of grease samples was performed using a digital scale with an accuracy of 0.1 mg. For each case, three different samples were prepared and tested.

The yield point and penetration values of grease sheared with and without water was measured using a rheometer, made by Anton Paar, model MCR 301. The rheometer of torque capacity 0.1-200 mN·m with a resolution of 0.001 pN·m and accuracy of 0.2 pN·m, load capacity in the range 0.005 to 50 N with a resolution of 0.002 N, accuracy ±0.03 N and the rotational speed of 10$^{-6}$ rpm-3000 rpm was employed for testing. The rheometer setup is shown in FIG. 1. The rheometer contains a driving motor connected with a rotating plate of ~25 mm diameter using a coupling. Air compressor of capacity 1.5 hp and 26 gallons, was used to supply the air to the motor. The experimental temperature was controlled using a temperature controller.

The yield point, considered as an indicator of a grease's consistency, is determined from the stress-strain plot. This plot is obtained by oscillate-sweeping the plate from 0.01 to 1 at a fixed frequency of 1 Hz on a grease sample thickness of 1 mm. From the stress-strain curve, the yield point is obtained using the procedure proposed by Cyriac et al. According to Cyriac et al., the yield point is the point where the coefficient of determination ($R^2$) between the third-order polynomial fit of the experimental values and linear fit, is greater than 99.5%. The level of degradation of the grease with water contamination is determined from the percentage difference in the yield stress properties $\tau_{diff}\%$ determined for both cases. The value of $\tau_{diff}\%$ is determined using Eq. (1) where $\tau_{pr}$ and $\tau_{con}$ are the yield stresses obtained for greases sheared without and with water, respectively.

In the next approach, greases samples are tested for change in penetration value. In this test, grease sample is squeezed between the plate and stationary surface of the rheometer with a normal force of 6 N for 5 s. The displacement of the plate is recorded for every second. The net penetration of grease is then determined by calculating the difference of the initial (1 mm) and final position of plate. In all the penetration tests, the temperature is maintained as 25° C. The percentage of degradation in grease with water contamination through penetration value $\delta\_diff\ \%$ is calculated from the penetration values obtained for greases shear without $\delta_{wo}$ and with $\delta_w$ water.

$$\delta_{diff}\% = \frac{(\delta_{wo} - \delta_w)}{\delta_{wo}} \times 100 \qquad (2)$$

In the present work, a drop shape analyzer shown in FIG. 3 was used to determine the contact angle of the water droplets on grease surface. This setup consists of camera (IDS UI-5480CP-M-GL GigE camera) and adjustable lens (Thorlabs AC254-075-A-ML Lens) to analyze a water droplet on a grease sample. Using an adjustable screw, the height of the sample stage is adjusted, such that the water droplet is in line to the lens height. The angle adjusting screw is used to adjust the angle of the lens. Monochromatic blue light helps in clearly distinguishing image of the droplet from the background. From the captured image, the contact angle θ may be calculated by the built-in software. The experimental setup associated with FIGS. 3-4D was used to analyze the droplets.

Due to semi-solid nature and complex structure of grease, the dimensions of the droplets on grease surface varies with time, making it difficult to capture the image instantaneously. To address these issues, videos of the droplet is recorded before the dropping of the droplet for more than 5 min at 3 frames/s. Images of water droplet from the video at different intervals is considered for measuring the contact angles.

In the present work, the values of contact angle from the water droplets are determined by measuring the length and breadth of a rectangle drawn manually around the edges and peak point of the droplet as described above and depicted in FIG. 8. On each type of grease, minimum of nine sets of readings are taken.

Figure 13:
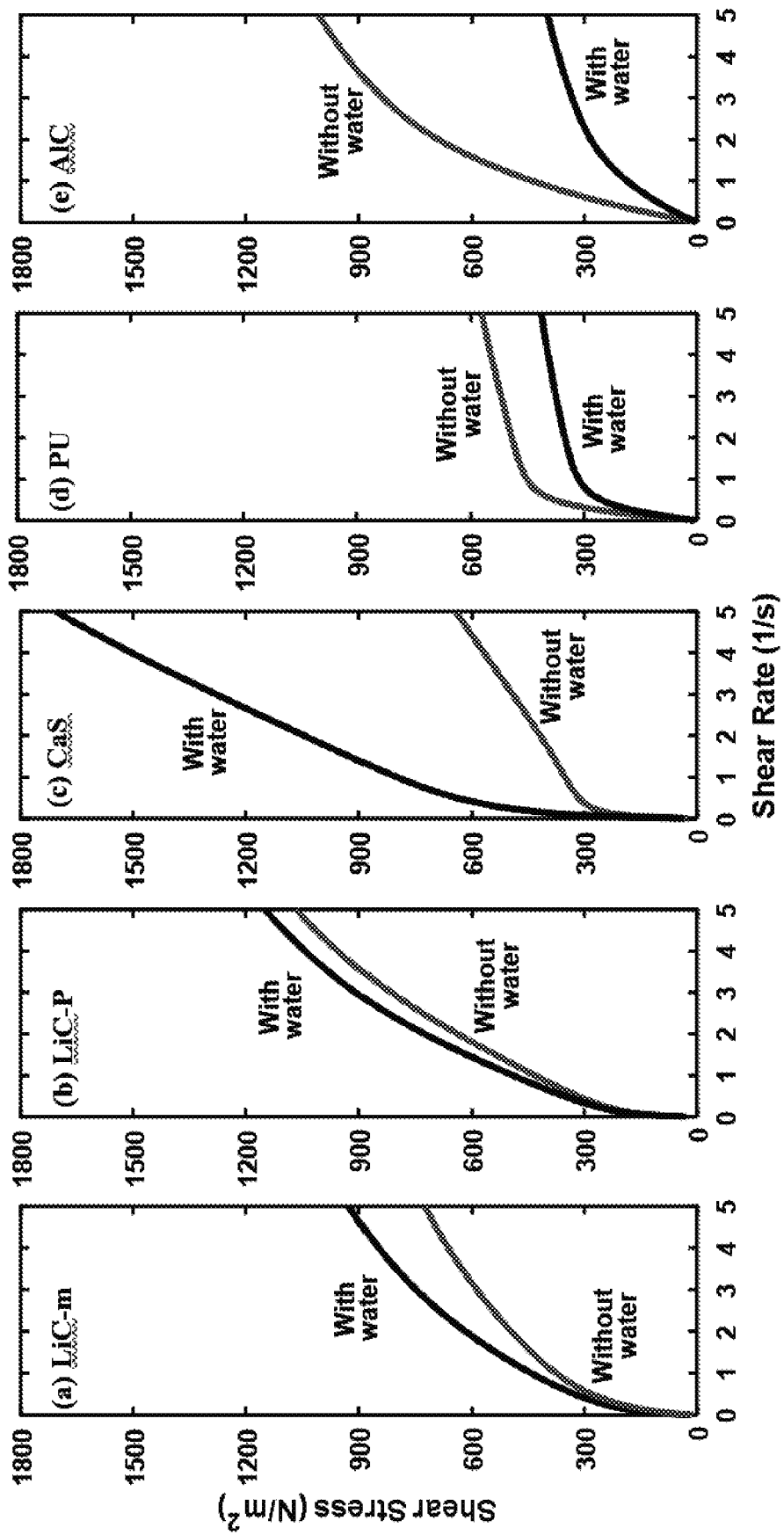
FIG. 13 is a shear stress plot for various water contaminated and uncontaminated greases.

To determine the yield stress values, the shear stress plots for LiC-m, LiC—P, CaS, PU, and AlC, greases were obtained from the oscillatory sweep experiments and plotted in FIG. 13, respectively. These figures reveal that the shear stress values obtained LiC-m, LiC—P and CaS greases without water is lower than when grease is contaminated with water, while FIG. 6 parts c and d, suggest an opposite trend for PU and AlC greases.

Figure 14A:
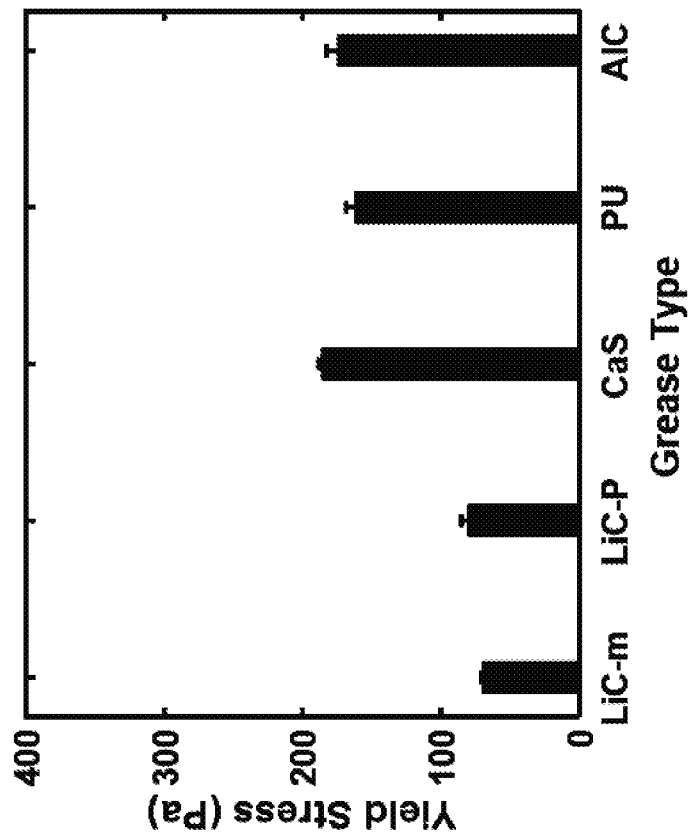
FIG. 14A depicts yield stress values without water contamination.
Figure 14B:
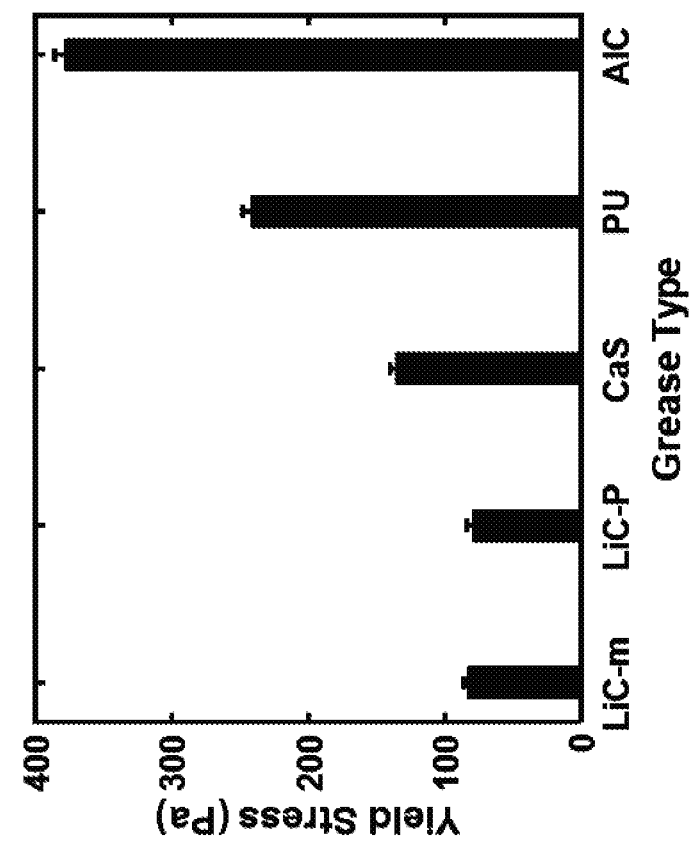
FIG. 14B depicts yield stress values with water contamination.

From the experimentally obtained shear stress-shear rate values and using the linear fit function in Matlab, the yield stress values are determined for $R^2>99.5\%$. The yield stress values calculated for all greases, which are sheared without and with water is plotted in FIGS. 14A and 14B, respectively.

Percentage difference in yield stress values calculated using Eq. (1) for different greases and the obtained values are shown in FIG. 15A. Similarly, from the penetration values obtained for grease sheared without and with water contamination, the percentage change due to the contamination of water is determined using Eq. (2). Determined values are plotted in FIG. 15B.

Figures 16A, 16B:
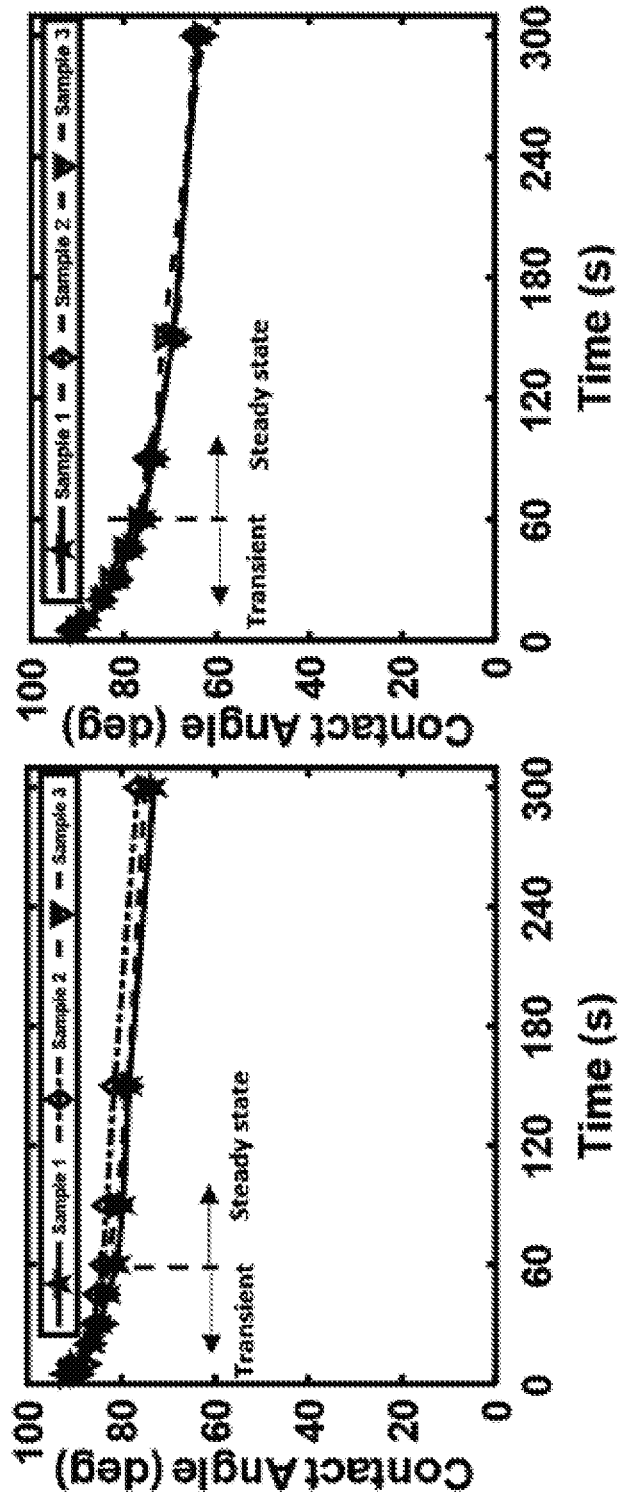
FIG. 16A depicts contact angle values obtained for LiC-m without water.
FIG. 16B depicts contact angle values for LiC-m with water.

Water droplets were recorded on the grease surface from initial placement and through the transformation of the droplet. From the recorded video, the images of the water droplets were captured at time interval of 5, 10, 20, 30, 45, 60, 150 and 300 s and the contact angle was measured on the captured images using the inbuilt software. The contact angle values obtained for LiC-m without water is shown in FIG. 16A. The contact angle values obtained for LiC-m with water is shown in FIG. 16B. The contact angle values obtained for PU greases without water is shown in FIG. 17A. The contact angle values obtained for PU greases with water is shown in FIG. 17B. Referring to these figures it can be inferred that there exists initial transient region followed by steady state region and the starting of steady state region is observed to be from about 60 s. It is interesting to note that the variation in the contact angle values among the samples are somewhat scattered during the first 45 s of the process but become invariant and "stabilize" thereafter. Evaluation of contact angle after 60 s can provide adequate information for practical purposes.

Figure 18:
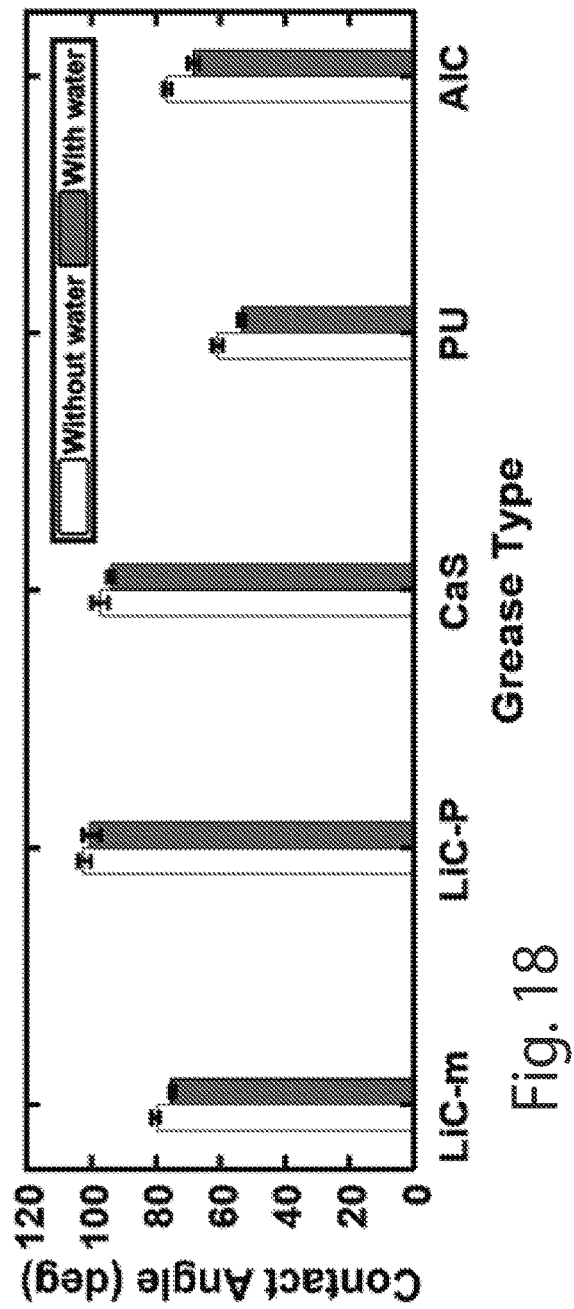
FIG. 18 depicts average contact angle values for greases with and without water.
Figure 19:
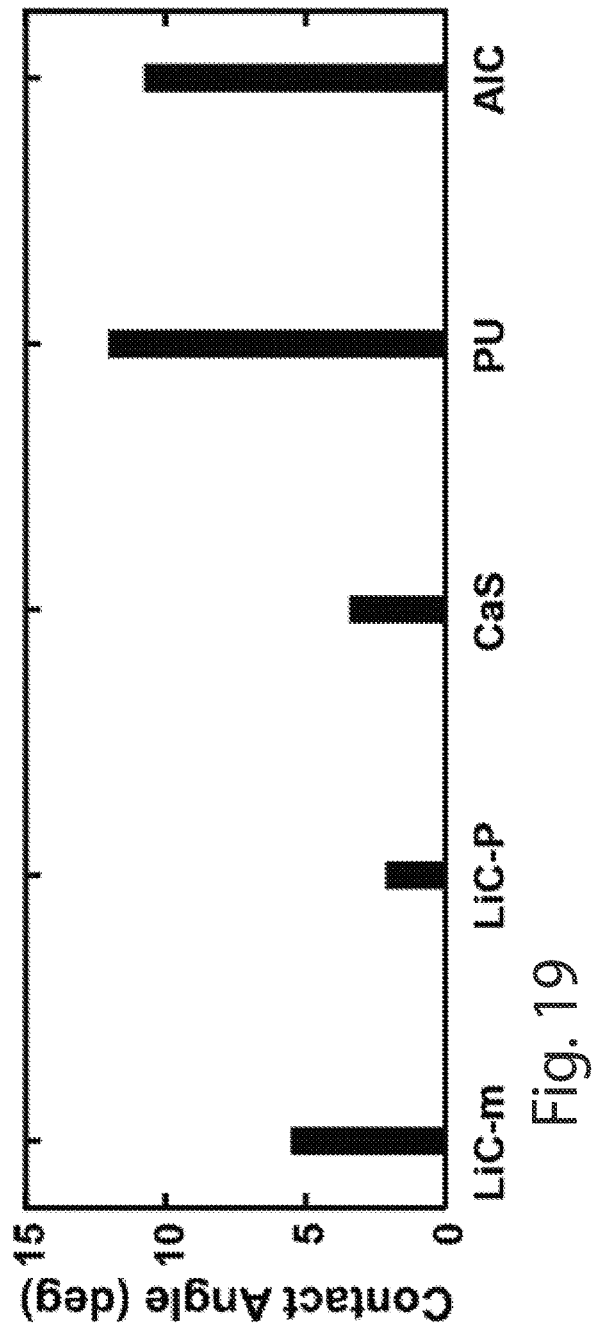
FIG. 19 depicts percentage changes in contact angle values with the water contamination.

The average values of contact angle at 60 s are determined for greases sheared in the absence and presence of water and plotted in FIG. 18. Observing this figure, it can be established that the contact angle values reduced with the water contamination. The percentage change in the contact angle values with the water contamination is determined using Eq. (2) and the values are shown in FIG. 19.

After shearing grease in grease worker for 10000 strokes with and without water, the samples from grease cup are considered for visual inspection. The pictures of the water contaminated greases along with worked greases without water is shown in FIG. 12.

For Greases LiC-m, LiC—P, and CaS, a clear distinction in color with water contamination is observed. The greases with water contamination are observed to be milkier and mushier than the uncontaminated grease. For Grease PU, the change in color is meager while in case of Greases AlC, no considerable distinction in appearance is observed with water contamination. It can be inferred that, this test exhibits difference in the appearance for few greases, however, for other greases, either it is very difficult or fails to display any difference. Therefore, it is conclusive that using the detection of change in color to determine contamination of grease by water may lead to wrong information to the practitioners.

Comparing FIGS. 15A and 15B, it can be concluded that, though the magnitude of change between the yield stress and penetration values are different, the trend in the variations is same, i.e., the change is observed positive for LiC-m, PU and AlC greases, while negative for LiC—P and CaS greases. These negative changes in yield stress indicates the thickening of greases in the presence of water while positive change indicated dilution of grease. Both positive and negative values in the rheological properties make the interpretation of grease resistance to water difficult for practitioners. It is not clear whether the test performance of the LiC-m, PU and AlC based greases perform better than LiC—P and CaS based greases.

The contact angle approach may be used to determine the polar active components on grease surface and correlate the values to water repelling properties of grease. The proposed approach requires a minimal quantity (~75 mm$^3$) of grease compared to rheometer method (490 mm$^3$). The contact angle values obtained for different intervals of time for LiC-m and PU greases sheared in the absence and presence of water for 10000 strokes are plotted in FIGS. 16A through 17B, respectively. From these figures it is observed that the contact angle values constantly reduced non-linearly until 60 s and linear reduction, thereafter, was observed. Therefore, the contact angle values at 60 s may have particular significance for evaluating the water repellent properties of grease. The average values of contact angle obtained for all greases sheared without and with water, at 60 s is plotted in FIG. 18. This figure suggests that the contact angle values reduced with the water contamination. The reduction in the contact angle values can be correlated to the presence of water in grease and making that grease more hydrophilic.

The percentage change in the contact angle values with the contamination of water is determined using Eq. (2) and the determined values are plotted in FIG. 19. Further, the change is observed to be less for LiC—P indicting a good water repellant grease while PU grease with high change indicating the poor water repellant. The order of water repellant properties can be consolidated as:

LiC—P>CaS>LiC-m>AlC>PU

Finally, from FIG. 19 it can be concluded that the optical contact angle evaluation methods described herein have the capability of providing the water repellant properties of greases in a single platform, which makes the practitioners easily distinguish a good or poor water repellant and select a grease for their application.

Figure 22:
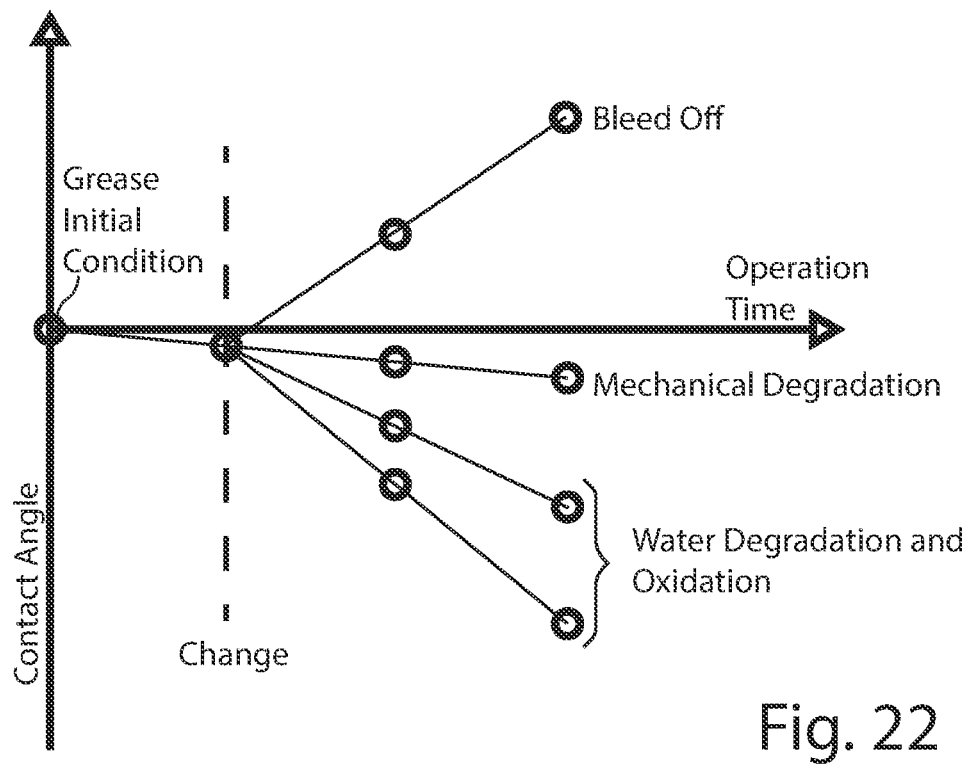
FIG. 22 depicts relative contact angle changes due to equipment operation.
Figure 23:
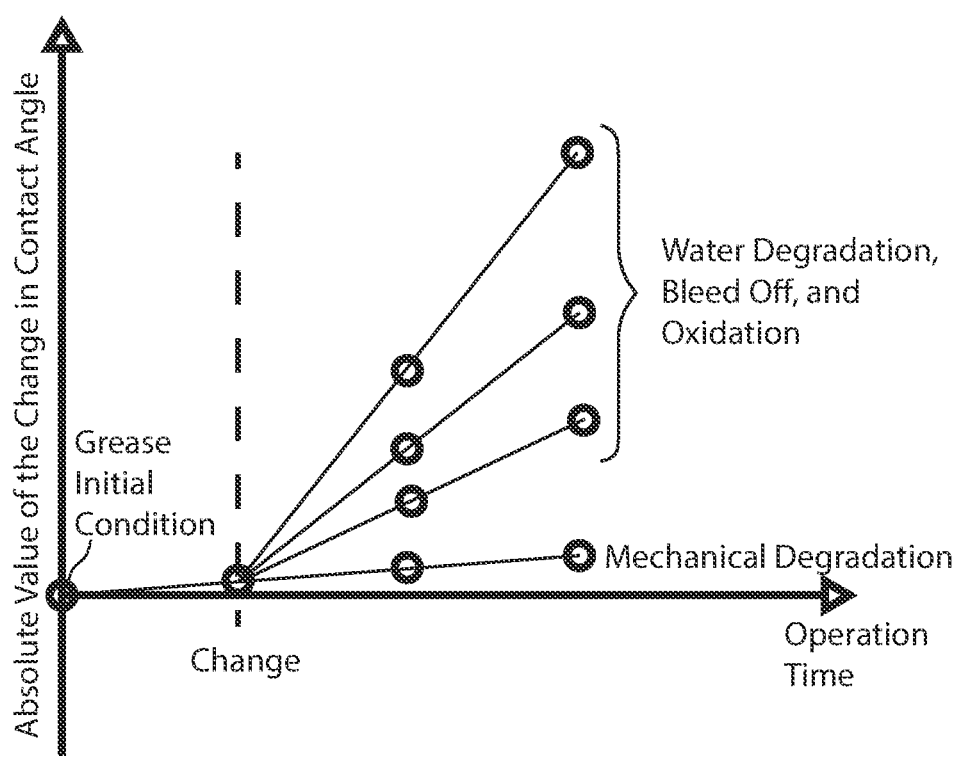
FIG. 23 depicts relative contact angle changes due to equipment operation in absolute value form.

In practice, the contact angle techniques described herein may be used to evaluate the operating conditions of both grease and the equipment that the grease is operating in. By evaluating the absolute change in the contact angle along with the direction of change of the contact angle a rate of degradation and a type of degradation may be established. Relatively speaking smaller and slower changes in the contact angle over the operational life of equipment or of a particular charge of grease may be attributed to mechanical degradation and other similar normal wear-based effects. FIG. 22 shows relative changes from an initial grease contact angle over the course of equipment operation for common forms of degradation. It has been shown that water degradation uniformly and significantly lowers the contact angle and may be used as a signal of problematic degradation of the grease. Conditions such as bleed off may similarly show departure from the initial contact angle of the grease during operation. Because bleed off is a significant compositional change, the magnitude of the change is likely to be greater than that of the minor changes due to the ordinary wear of grease in normal operation. The contact angle may increase as is shown in FIG. 22. The direction of the change in the contact angle may be used as a piece of evidence in the diagnosis of problems with machinery. For example, the direction of change in contact angle may be a signal of water intrusion or of operational problems associated with grease bleed off. Each type of degradation and compositional change in the grease is expected to impact the contact angle of the grease associated with the measurements described herein. For that reason, the absolute value of the deviation from the contact angle of the pristine grease may be used as a general metric for the degradation of grease. As shown in FIG. 23 the most concerning types of degradation are likely to show the greatest absolute value change in contact angle from pristine grease making the contact angle technique a potentially powerful indicator of the overall health of a grease system. Persons evaluating the condition of grease and associated equipment may therefore use the numbers associated with these tests to make decisions about the replacement of grease and to make decisions about the replacement and maintenance of equipment. The relative degradation of the grease with water contamination and bleed off is subjective to the grease types and depends on the chemistry of the grease. As some greases may have (i) good water resistance but poor bleed off properties, or (i) bad water resistance but with good bleed off property, or (iii) both properties are inferior or (ii) both are superior, FIGS. 22 and 23 should be considered examples rather than representative of all grease.

Consistent with the teachings of FIG. 22, relationships between contact angle and degradation will commonly proceed according to the following trends: (i) If the contact angle value for pristine grease is 'x' then a contact angle for mechanical degraded grease 'y', will tend to follow the relationship x>y; (ii) if the grease is operated in the water contaminated environment, and the measured contact angle of that grease is 'z', then (x>y>z) is likely; and (iii) if grease bleed off occurs at room temperature due to high pressure and the measured contact angle of that grease is 'a', then (a>x>y) is likely.

Techniques described herein may be used for greases at elevated temperatures where oxidation occurs. In these situations, the oxidative degradation will generally lower the contact angle.

Example Set 3

Referring to FIGS. 20A, 20B, 20C, 21A, and 21B, a Portable measuring device 300 may include: Base 310, Monochromatic light source 320, Camera 330, Grease assembly 340, Grease assembly stand 343, Grease support 345, Grease collar 346, Grease collar upper surface 347, Grease slot 348, Testing grease 380, Testing grease top surface 383, Grease wiper 390, Grease wiper support 393, and Grease wiper stepper motor 396.

Portable measuring device 300 allows for the convenient contact angle testing of grease samples from machinery and may be transported for on the spot testing of grease samples from the machinery. It allows the practitioners to take the device to several sites for testing the samples.

When Grease collar 346 is in its upward position as depicted in FIG. 20A, Testing grease 380 may be filled into Grease slot 348 with excess grease to be wiped away and the grease may be scraped with a level wiper such as Grease wiper 390 using a rotating motion such that Testing grease top surface 383 becomes level with Grease collar upper surface 347. Grease collar 346 may move up and down relative to Grease support 345 and that relative motion may, for example, be by way of a threaded relationship between Grease collar 346 and Grease support 345. The configuration in which Grease collar 346 is in its upward position as depicted in FIG. 20A, allows for the accurate creation of a smooth Testing grease top surface 383. The transition through an intermediate position, shown in FIG. 20B, to a lowered position, shown in FIG. 20C, allows for the presentation of a clean Testing grease top surface 383 between Monochromatic light source 320 and Camera 330 without any obstruction by Grease assembly 340. This procedure provides a uniform thickness of the grease for testing and a constant base line for evaluating the contact angle. Grease collar 346 may be configured such that it has a hard stop at its upper extent of travel and a hard stop at the lower extent of travel to enhance the consistency of test results. Grease support 345 supports Testing grease 380 throughout the preparation and testing.

The wiping or scraping of grease may be done by Grease wiper 390 which may be driven by Grease wiper stepper motor 396 which is supported by Grease wiper support 393. The automated wiping process may lead to greater consistency and smoothness of Testing grease top surface 383.

On the grease surface, a water droplet may be placed using a 10 μl syringe, and the image of the droplet may be captured using Camera 330. Monochromatic blue light may be provided by Monochromatic light source 320 to achieve a clear black image of the droplet. The captured image may be wirelessly transferred to a phone, computer, or other device and the contact angle θ may then be calculated.

Evaluations of contact angle may be done against pristine grease or against reference values. The evaluations and comparisons may be done manually, by the testing machine, or by some other device. Molds with multiple grease slots for testing grease may be used as an alternative to the single slot device.

Contact angle techniques described herein may be used to evaluate the operating conditions of both grease and grease lubricated machines. By evaluating the values of contact angles, absolute values of changes in the contact angle, and the direction of change of the contact angle degrees of degradation may be established and potential causes of degradation may be evaluated.

Grease may degrade in single mode which may be detectable by the methods described herein such as: grease operated below 50° C. without other contaminations due to mechanical shearing, degradation due to water contamination, thermal degradation in high temperature idle equipment, and oil separation/leakage during grease storage. The magnitude of the degradation due to single mode of degradation will vary based on the type of grease. Degrees of degradation may vary from grease to grease, machine to machine, and application to application. Developing data by testing the grease in different operating/environment conditions and providing the contact angle values for different modes of degradation for a particular developed grease, could help the user in both selecting the grease for their application and evaluating the level of degradation of used grease.

While the techniques described herein generally refer to grease as the substance being tested, additional substances having viscosities and consistencies in the range of NLGI consistencies from 000 to 6 may be tested as well. In particular, consistencies from grade 0 to grade 4 may be tested using these techniques. One such substance is peanut butter.

As the phrase is used herein 'mechanically used grease' designates a finished grease, namely a grease that has completed preparations for use as a lubricant, that has been used in a machine or mechanical component as a lubricant for some period of time.

The term 'absorb' and its related forms is used herein to broadly denote various forms of incorporation that include both chemical adsorption and chemical absorption.

Methods of characterizing grease may for example comprise: taking a grease sample; using a guide to create a volume of grease having a planar grease surface; arranging the planar grease surface to be level and aligned with the lens of a camera; placing a drop of water on the planar grease surface creating an initial contact angle; allowing a first portion of the drop of water to be absorbed by the volume of grease over a period of time thereby creating an altered drop of water having a subsequent contact angle; capturing an image of the altered drop of water; and calculating the subsequent contact angle. In certain examples, the procedure may include observing the time dependent change in droplet characteristics. The period of time may be greater than 20 seconds. The grease sample may be less than 490 mm$^3$. The grease sample may be less than 8000 mm$^3$. This procedure may be repeated for a piece of equipment such that an absolute change from the measured contact angle of a new grease is evaluated to determine an extent to which the grease may be compromised. The procedure may be repeated for a piece of equipment such that a rate of change from the measured contact angle of the operating grease in a piece of equipment is evaluated to determine the rate of degradation of the grease in the equipment over the life of the equipment. The above procedure may be repeated to evaluate the statistical characteristics of multiple samples of grease from an individual piece of equipment and that statistical information may be used to evaluate the degradation of the grease. The above procedure may be repeated for a piece of equipment such that the direction of change from the measured contact angle of the operating grease in a piece of equipment is evaluated to determine the manner of grease degradation during the life of the life of the equipment.

Methods of evaluating lubricants, may for example comprise: acquiring a sample of a mechanically used grease from a mechanical device; preparing a grease surface for testing by orienting a portion of the sample to level and flattening the portion of the sample; placing a drop of a liquid on the grease surface; evaluating an observed contact angle between the drop and the grease surface; and comparing the observed contact angle to a reference contact angle; wherein the mechanically used grease is degraded as compared to a pristine grease of the same type. In a related example, the mechanically used grease may have experienced bleed off as compared to the pristine grease of the same type. In a related example, the mechanically used grease may have experienced oxidation as compared to the pristine grease of the same type. In a related example, the mechanically used grease may have experienced mechanical degradation as compared to the pristine grease of the same type. In a related example, the mechanically used grease may have experienced contamination as compared to the pristine grease of the same type. In a related example, the mechanically used grease may have experienced water contamination as compared to the pristine grease of the same type. In a related example, the observed contact angle may correlate with the kinematic viscosity of the mechanically used grease across varying degradation levels for a degradation type wherein the degradation type is selected from bleed off, mechanical degradation, and water degradation. In a related example, the observed contact angle may correlate with the dynamic viscosity of the mechanically used grease across varying degradation levels for a degradation type wherein the degradation type is selected from bleed off, mechanical degradation, and water degradation. In a related example, the observed contact angle may correlate with the yield stress of the mechanically used grease across varying degradation levels for a degradation type wherein the degradation type is selected from bleed off, mechanical degradation, and water degradation. In a related example, the observed contact angle may correlate with the cross over stress of the mechanically used grease across varying degradation levels for a degradation type wherein the degradation type is selected from bleed off, mechanical degradation, and water degradation. In a related example, the observed contact angle may correlate with the grease consistency grade of the mechanically used grease across varying degradation levels for a degradation type wherein the degradation type is selected from bleed off, mechanical degradation, and water degradation. In a related example, the further step of taking a maintenance action based on the comparing of the observed contact angle to the reference contact angle may occur. In a related example, the drop of the liquid may undergo a non-steady state mass transfer with the portion of the sample prior to the evaluating of the observed contact angle. In a related example, the evaluating of the observed contact angle may take place during a substantially steady-state mass transfer from the drop to the portion of the sample. In a related example, the observed contact angle may be higher than the reference contact angle and bleed off has occurred in the mechanically used grease. In a related example, the observed contact angle may be lower than the reference contact angle and a form of degradation has occurred in the mechanically used grease and the form of degradation is selected from mechanical degradation and water contamination. In a related example, the observed contact angle may be lower than the reference contact angle and degradation from oxidation has occurred. In a related example, the observed contact angle may correlate with a volumetric property of the semi-solid composition. In a related example, flattening of the portion of the sample may include exposing an internal portion of the sample at the grease surface.

Methods of evaluating properties may, for example, include: acquiring a sample of a semi-solid composition; preparing a composition surface for testing by: positioning a first portion of the sample and a second portion of the sample in a container, scraping the second portion of the sample from the first portion of the sample thereby removing the second portion of the sample from the first portion of the sample, and leveling an item selected from the composition surface and the container, wherein the scraping of the second portion of the sample from the first portion of the sample exposes an internal portion of the sample at the composition surface, and wherein the scraping of the second portion of the sample from the first portion of the sample creates a flattened surface of the semi-solid composition; placing a drop of a liquid on the composition surface; and evaluating an observed contact angle between the drop and the composition surface; wherein the observed contact angle correlates with a volumetric property of the semi-solid composition.

References herein to grease consistency grade refer to consistency grading standards established by the National Lubricating Grease Institute NLGI.

As that phrase is used herein, "volumetric property" refers to properties of a substance that are present within a volume of that substance such as viscosity and yield stress. Volumetric property does not refer to properties of a surface.

Types of degradation which may be detected by contact angle measurements described herein include physical degradation, which may include bleed off; mechanical degradation, which may include grease shearing and chain breaking; chemical degradation, which may include oxidation; and contamination, which may include liquid contamination such as water contamination and solid contamination such as particulate matter which may include one or more of sand, dust, and metal.

The above-described embodiments have a number of independently useful individual features that have particular utility when used in combination with one another including combinations of features from embodiments described separately. There are, of course, other alternate embodiments which are obvious from the foregoing descriptions, which are intended to be included within the scope of the present application.

The invention claimed is:

1. A method of evaluating properties comprising:
   a. acquiring a sample of an additive modified peanut butter;
   b. preparing a sample surface for testing by:
      i. positioning a first portion of the sample and a second portion of the sample in a container,
      ii. scraping the second portion of the sample from the first portion of the sample thereby removing the second portion of the sample from the first portion of the sample, and
      iii. leveling an item selected from the sample surface and the container,
      iv. wherein the scraping of the second portion of the sample from the first portion of the sample exposes an internal portion of the sample at the sample surface, and
      v. wherein the scraping of the second portion of the sample from the first portion of the sample creates a flattened surface of the additive modified peanut butter;
   c. placing a drop of a liquid on the sample surface; and
   d. evaluating an observed contact angle between the drop and the sample surface;
   e. wherein the observed contact angle correlates with a volumetric property of the additive modified peanut butter.

2. The method of claim 1 wherein the additive modified peanut butter is thickened as compared to an equivalent non-additive modified peanut butter of the same type.

3. The method of claim 1 wherein the additive modified peanut butter changes consistency grades as compared to an equivalent non-additive modified peanut butter of the same type.

4. The method of claim 1 wherein the observed contact angle correlates with the kinematic viscosity of the additive modified peanut butter.

5. The method of claim 1 wherein the observed contact angle correlates with the dynamic viscosity of the additive modified peanut butter.

6. The method of claim 1 wherein the observed contact angle correlates with the yield stress of the additive modified peanut butter.

7. The method of claim 1 wherein the observed contact angle correlates with the cross over stress of the additive modified peanut butter.

8. The method of claim 1 wherein the observed contact angle correlates with the consistency grade of the additive modified peanut butter.

9. The method of claim 1 further comprising making a decision to continue or stop additive inclusion based on the comparing of the observed contact angle to a reference contact angle.

10. The method of claim 1 wherein the drop of the liquid undergoes a non-steady state mass transfer with the first portion of the sample prior to the evaluating of the observed contact angle.

11. The method of claim 1 wherein the evaluating of the observed contact angle takes place during a substantially steady-state mass transfer from the drop to the first portion of the sample.

12. The method of claim 1 wherein the observed contact angle is lower than a reference contact angle.

13. The method of claim 1 wherein the observed contact angle is higher than a reference contact angle.

* * * * *